US008697714B2

(12) United States Patent
Xing et al.

(10) Patent No.: US 8,697,714 B2
(45) Date of Patent: Apr. 15, 2014

(54) QUINAZOLINONE BASED FLUOROGENIC PROBES

(75) Inventors: Bengang Xing, Singapore (SG); Junxin Aw, Singapore (SG); Qing Shao, Singapore (SG); Yanmei Yang, Singapore (SG); Tingting Jiang, Singapore (SG); Chungyen Ang, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/193,101

(22) Filed: Jul. 28, 2011

(65) Prior Publication Data

US 2012/0288884 A1 Nov. 15, 2012

Related U.S. Application Data

(60) Provisional application No. 61/368,504, filed on Jul. 28, 2010.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............... 514/266.2; 514/266.1; 544/283; 544/284

(58) Field of Classification Search
USPC ............... 514/266.2, 266.1; 544/283, 284
See application file for complete search history.

(56) References Cited

U.S. PATENT DOCUMENTS 5,316,906 A 5/1994 Haugland et al.
2008/0194522 A1 8/2008 Chen et al.

OTHER PUBLICATIONS

Abeles, R. H. et al., *Suicide Enzyme Inactivators*, Accounts of Chemical Research, vol. 9, No. 9, (1976), pp. 313-319
Albers, A. E. et al., *Activity Based Fluorescent Reporters for Monoamine Oxidases in Living*, Chem. Commun., (2007), pp. 4647-4649
Berge, S. M. et al., *Pharmaceutical Salts*, Journal of Pharmaceutical Sciences, vol. 66, No. 1, (1977), pp. 1-19.
Binda, C. et al., *Structures of Human Monoamine Oxidase B Complexes with Selective Noncovalent Inhibitors: Safinamide and Coumarin Analogs*, J. Med Chem., 50, (2007), pp. 5848-5852.
Bisset, P. et al., *Synthesis and Biological Evaluation of MIAO-A Selective 1,4-Disubstituted-1,2,3,6-tetrahydropyridinyl Substrates*, Bioorganic & Medicinal Chemistry, 10, (2002), pp. 3031-3041.
Cai, W. et al., *Imaging of Integrins as Biomarkers for Tumor Angiogenesis*, Current Pharmaceutical Design, 14, (2008), pp. 2943-2973.
Chen, G. et al., *Design of Optical Switches as Metabolic Indicators: New Fluorogenic Probes for Monoamine Oxidases (MAO A and B)*, J. Am. Chem. Soc., 127, (2005), p. 4544-4545.
Chen, I. et al., *Site-specific Labeling of Proteins With Small Molecules in Live Cell*, Current Opinion in Biotechnology, 16, (2005), pp. 35-40.
Cheng, Z. et al., *Near-Infrared Fluorescent Deoxyglucose Analogue for Tumor Optical Imaging in Cell Culture and Living Mice*, Bioconjugate Chem., 17, (2006), pp. 662-669.
Choi, Y. H. et al., *Polyethylene Glycol-Grafted Poly-L-lysine as Polymeric Gene Carrier*, Journal of Controlled Release, 54, (1998), pp. 39-48.
Diwu, Z. et al., *Fluorescent Molecular Probes I. The Synthesis and Biological Properties of an ELF® β-glucuronidase Substrate That Yields Fluorescent Precipitates at the Enzymatic Activity Sites*, Tetrahedron, vol. 53, No. 21, (1997), pp. 7159-7164.
Edmondson, D. E. et al., *Structure and Mechanism of Monoamine Oxidase*, Current Medicinal Chemistry, 11, (2004), pp. 1983-1993.
Feng, F. et al., *Continuous Fluorometric Assays for Acetylcholinesterase Activity and Inhibition with Conjgated Polyelectrolytes*, Angew. Chem. Int. Ed., 46, (2007), pp. 7882-7886.
Funovics, M. et al., *Protease Sensors for Bioimaging*, Anal Bioanal Chem, 377, (2003), 956-963.
Holt, A. et al., *A continuous Spectrophotometric Assay for Monoamine Oxidase and Related Enzymes in Tissue Homogenates*, Analytical Biochemistry, Article No. AB969911, 244, (1997), pp. 384-392.
Holt, A. et al., *Metabolism of Agmatine (clonidine-displacing substance) by Diamine Oxidase and the Possible Implications for Studies of Imidazoline Receptors*, Chapter 19, Progress in Brain Research, vol. 106, (1995), pp. 187-197.
Huang, Z. et al., *2-(2'-Phosphoryloxyphenyl)-4(3H)-Quinazolinone Derivatives as Fluorogenic Precipitating Substrates of Phosphatases[1]*, Analytical Biochemishl, 207, (1992), pp. 32-39.
Ishikawa, E., *Enzyme Immunoassay of Insuline by Fluorimetry of the Insulin-Glucoamylase Complex*, J. Biochem., 73, (1973), pp. 1319-1321.
Jefferson, R. A., *The GUS Reporter Gene System*, Nature, vol. 342, (1989), pp. 837-838.
Kalgutkar, A. S. et al., *Interactions of Nitrogen-Containing Xenobiotics With Monoamine Oxidase (MAO) Isozymes A and B: SAR Studies on MAO Substrates and Inhibitors*, Chemical Research in Toxicology, vol. 14, No. 9, (2001), pp. 1140-1162.
Kamiya, M. et al., *An Enzymatically Activated Fluorescence Probe for Targeted Tumor Imaging*, J. Am. Chem. Soc., 129, (2007), pp. 3918-3929.
Kohda, K. et al., *Cytotoxicity of 1-Amino-4-phenyl-1,2,3,6-tetrahydropyridine and 1-Amino-4-phenylpyridinium Ion, 1-Amino Analogues of MPTP and MPP+, to clonal Pheochromocytoma PC12 Cells*, Chem. Res. Toxicol., 11, (1998), pp. 1249-1253.
Lavis, L. D. et al., *Fluorogenic Label for Biomolecular Imaging*, ACS Chemical Biology, vol. 1, No. 4, (2006), pp. 252-260.
Levant, B., *Novel Drug Interactions at $D_2$ Dopamine Receptors: Modulation of [$^3$H ] quinpirole Binding by Monoamine Oxidase Inhibitors*, Life Sciences, 71, (2002), pp. 2691-2700.
Maeda, H. et al., *2,4-Dinitrobenzenesulfonyl Fluoresceins as Fluorescent Alternatives to Ellman's Reagent in Thiol-quantification Enzyme Assays\*\**, Angew. Chem. Int. Ed., 44, (2005), pp. 2922-2925.

(Continued)

*Primary Examiner* — Paul V. Ward
(74) *Attorney, Agent, or Firm* — Alston & Bird LLP

(57) ABSTRACT

The present invention relates to a compound of the general formula (I) useful in the determining the presence, amount or activity of an enzyme in living cells, a method of preparing said compounds and a kit thereof.

18 Claims, 10 Drawing Sheets

(56) References Cited

OTHER PUBLICATIONS

Mandel, S. et al., *Mechanism of Neuroprotective Action of the Anti-Parkinson Drug Rasagiline and Its Derivatives*, Brain Research Reviews, 48, (2005), pp. 379-387.

Mucsi, Z. et al., *Modeling Rate-Controlling Solvent Effects. The Pericyclic Meisenheimer Rearrangement of N-Propargylmorpholine N-Oxide*, J. Am. Chem. Soc., 127, (2005), pp. 7615-7631.

Olanow, C. W., *Rationale for Considering that Propargylamines Might be Neuroprotective in Parkinson's Disease*, Neurology 66(Suppl 4), (2006), pp. 869-879.

Ravni, A. et al., *The Neurotrophic Effects of PACAP in PC12 Cells: control by Multiple Transduction Pathways*, Journal of Neurochemistry, 98, (2006), pp. 321-329.

Shih, J. C. et al., *Monoamine Oxidase: From Genes to Behavior*, Annu. Rev. Neurosci., 22, (1999), pp. 197-217.

Silverman, R. B., *Radical Ideas About Monoamine Oxidase*, Acc. Chem. Res., 28, (1995), pp. 335-342.

Terai, T. et al., *Fluorescent Probes for Bioimaging Applications*, Current Opinion in Chemical Biology, 12, (2008), pp. 515-521.

Tsien, R. Y., *Imagining Imaging's Future*, Imaging in Cell Biology, Nature Publishing Group, (2003), pp. SS16-SS21.

Uttamchandani, M. et al., *Next Generation Chemical Proteomic Tools for Rapid Enzyme Profiling*, Accounts of Chemical Research, vol. 42, No. 8, (2009), pp. 1183-119.

Webster, J. M. et al., *Engineered Two-Helix Small Proteins for Molecular Recognition*, ChemBioChem, 10, (2009), pp. 1293-1296.

Xing, B. et al., *Novel Beta-Lactam Antibiotics Derivatives: Their New Applications as Gene Reporters, Antitumor Prodrugs and Enzyme Inhibitors*, Mini-Reviews in Medicinal Chemistry, 8, (2008), pp. 455-471.

Youdim, M. B. H. et al., *Contrasting Monoamine Oxidase Activity and Tyramine Induced Catecholamine Release in PC12 and Chromaffin Cells*, Neuroscience, vol. 19, No. 4, (1986), pp. 1311-1318.

Youdim, M. B. H. et al., *The therapeutic Potential of Monoamine Oxidase Inhibitors*, Nature Reviews | Neuroscience, vol. 7, (2006), pp. 295-309.

Zhang, J. et al., *Creating New Fluorescent Probes for Cell Biology*, Nature Reviews, Nature Publishing Group, vol. 3, (2002), pp. 906-918.

Zhang, X. et al., *An Autoimmolative Spacer Allows First-Time Incorporation of a Unique Solid-State Fluorophore into a Detection Probe for Acyl Hydrolases*, Chem. Eur. J., 16, (2010), pp. 792-795.

Zhou, J. J. P. et al., *Direct Continuous Fluorometric Assay for Monoamine Oxidase B*, Analytical Biochemistry, Article No. 0041, 234, (1996), pp. 9-12.

Zhou, M. et al., *A Fluorogenic Substrate for β-glucuronidase; Application in Fluorometric, Polyacrylamide Gel and Histochemical Assays*, J. Biochem. Biophys. Methods, 33, (1996), pp. 197-205.

Zhou, W. et al., *New Bioluminogenic Substrates for Monoamine Oxidase Assays*, J. Am. Chem. Soc., 128, (2006), pp. 3122-3123.

QUINAZOLINONE BASED FLUOROGENIC PROBES

CROSS-REFERENCE TO RELATED APPLICATION

This application makes reference to and claims the benefit of priority of an application for a "Novel Fluorogenic Probes For Monoamine Oxidases in Living Cells" filed on Jul. 28, 2010 with the United States Patent and Trademark Office, and there duly assigned Ser. No. 61/368,504. The contents of said application filed on Jul. 28, 2010 is incorporated herein by reference for all purposes, including an incorporation of any element or part of the description, claims or drawings not contained herein.

FIELD OF THE INVENTION

The present invention relates to the field of fluoroprobes useful in the molecular imaging of enzyme activity in living cells.

BACKGROUND OF THE INVENTION

Optical imaging techniques such as fluorescence and bioluminescence imaging which use light source at different wavelengths for image generation, provide a simple and direct visualization of specific molecular targets or biological pathways in vitro and in vivo. Fluorescent technique requires the use of small molecule reporters such as fluorogenic probes which provide a measurable optical signal for a particular enzyme facilitated molecular process. Fluorescent detection is more advantageous in compared to colorimetric or radioisotope assay due to its high sensitivity, relative safety, low cost and easy handling. Therefore, imaging of metabolic and signaling events in live cells represent an important frontier in this field of fluoroprobes.

Certain probes can consist of fluorogenic or fluorescent dyes coupled to a blocking group thus forming an enzyme substrate. These probes are cleavable by enzymes, and produce fluorescent dye precipitates, which may be detected by fluorescence microscopy. For example, fluorogenic substrates can be detected by hydrolases which may be used in enzyme labeled fluorescence assays, where the fluorescence is used to detect enzyme activity. Examples of known fluorogenic substrates include 4-methylumbelliferyl β-D-galactoside for detecting β-D-galactosidase (GAL) enzyme activity and 4-methylumbelliferyl β-D-glucuronide for detecting β-D-glucuronidase (GUS) enzyme activity (Ishikawa E. et al, *J. Biochem* 73, 1319-1321, 1973; Jefferson R. A. *Nature*, 342, 837-838, 1989). Other fluorogenic substrates that are made from a class of fluorophores generally including quinazolinonoes for example, can be enzymatically converted to a detectable phenolic product, e.g. formation of a soluble coloured or fluorescent product or formation of a precipitate. For example, U.S. Pat. No. 5,316,906 describes such a substrate which consists of substances coupled with phosphate, sulfate or sugar groups and which form a highly fluorescent precipitate upon reaction with an appropriate enzyme. Particular examples of these substrates include ELF97® β-D-galactosidase substrate (ELF97® β-D-galacto-pyranoside) and ELF97® β-D-glucuronide that are commercially available.

However, the potential disadvantages of known fluorogenic substrates are their limited permeability for cell membranes and higher background caused by the autofluorescence of cell and tissue and unstable substrates. As a result, GUS and GAL assays are generally destructive for cells since the cells need to be permeabilized prior to detection of an intracellular analyte, and are thereof not suitable under in vivo conditions, or under in vitro conditions where cell integrity is desired. Many other substrates are not photostable, such as fluorescein, which bleaches after a few minutes, losing the fluorescence necessary for detection.

Monoamine oxidases (MAOs) are essential FAD-dependent enzymes in the living systems and play an essential role in the regulation of monoamine neurotransmitters such as dopamine and serotonin. It can efficiently catalyze the oxidation deamination of neuro transmitters and biogenic amines, to the corresponding imines which are released from the enzyme and hydrolyzed to the corresponding aldehydes. There are two isoforms, MAO A and MAO B, found large in abundant in the liver, gastrointestinal tract, blood platelets and central nervous systems. These enzymes play an important role in metabolism and neural development by regulating the homeostasis of amine neurotransmitters and periphery dietary amines. Any excess or deficiency of these enzyme activities will lead to various neurological and psychiatric disorders such as depression, Parkinson, Alzheimers's diseases or even the growth inhibition and progression of cancer. As such, development of suitable MAOs assays which enable selectively and sensitively monitoring of enzyme activities in complex biological system is of a highly fundamental necessity.

Despite its importance, currently available methods to monitor monoamine oxidase activity involving the use of colorimetric, radioisotope, require a secondary activating enzyme to release the signal for the detection or do not provide single-cell enzyme imaging. A fluorescence probe based on a coumarin derivative for detecting monoamine oxidase activity has been developed (see US Publication 2008/0194522), However, the possible photodamage, relative higher autofluorescence from most cell and tissue would be the potential issues for the further living cell studies. Although several methods based on fluorescent and bioluminescent detection have been developed in monitoring MAO activities, till date no report has been made in providing a direct and sensitive, real time imaging of MAO in living cells systems.

Therefore, it is an object of the present invention to provide an alternative fluorogenic probe which can efficiently detect enzyme activity in living cell systems.

The object is solved by a compound of general formula (I) as defined in the appended claims.

SUMMARY OF THE INVENTION

In one aspect, the invention provides a compound of general formula (I)

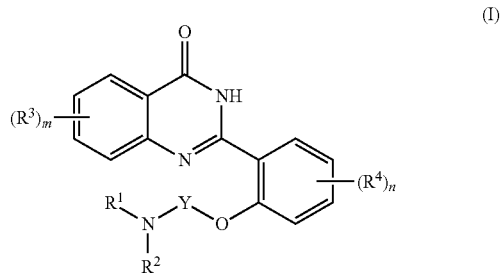

or a salt, tautomer or stereoisomer thereof. In the compound of general formula (I), $R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl; each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_6$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR'; Y is an aliphatic group; R and R' are independently selected from the group consisting of hydrogen and unsubstituted $C_1$-$C_4$ alkyl; and m and n are integers independently selected from 1, 2, 3 and 4.

In another aspect the invention provides a method for determining the presence, amount or activity of a monoamine oxidase. The method includes: i) contacting at least one compound as described herein with the monoamine oxidase under conditions that allow the oxidative deamination of the compound by the monoamine oxidase; and ii) determining the fluorescence of the compound.

In a further aspect the invention provides a method of preparing the compound of general formula (I) as described herein including: reacting a compound of general formula (II)

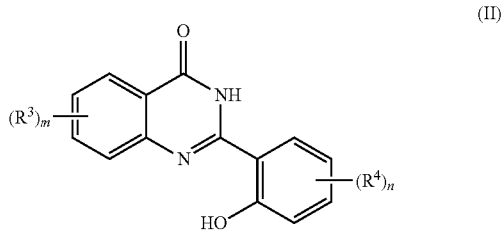

(II)

or a salt, tautomer or stereoisomer thereof,
wherein each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_6$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR'; R and R' are independently selected from the group consisting of hydrogen and unsubstituted $C_1$-$C_4$ alkyl; and m and n are integers independently selected from 1, 2, 3 and 4;
with a compound of general formula (III)

(III)

wherein $R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl; Y is an aliphatic group; and X is halogen; in the presence of a base.

In yet another aspect the invention provides a kit for the detection of the presence or amount of a monoamine oxidase comprising at least one compound described herein.

BRIEF DESCRIPTION OF THE DRAWINGS

The invention will be better understood with reference to the detailed description when considered in conjunction with the non-limiting examples and the accompanying drawings, in which:

FIG. 2a) shows the fluorescent enhancement of a compound according to one embodiment, 2(5'-chloro-2'-(3-aminopropoxy)phenyl)-6-chloro-4(3H)-quinazolinone ("MAO-HPQ 1") with MAO A. FIG. 2b) shows the fluorescent enhancement of 2-(5% chloro-2'-(3-aminopropoxy)phenyl)-6-chloro-4(3H)-quinazolinone ("MAO-HPQ 1") of the present invention with MAO B. FIG. 2c) shows the fluorescent enhancement of a compound according to one embodiment, 2-(5'-chloro-2'-(3-(N-methylamino)propoxy)phenyl)-6-chloro-4(3H)-quinazolinone ("MAO-HPQ 2") with MAO A. FIG. 2d) shows the fluorescent enhancement of a compound according to one embodiment, 2-(5'-chloro-2'-(3-(N-methylamino)propoxy)phenyl)-6-chloro-4(3H)-quinazolinone ("MAO-HPQ 2") with MAO B. FIG. 2e) shows the fluorescent enhancement of a compound according to one embodiment, 2-(5'-chloro-2'-(3-(N,N'-dimethylamino)propoxy)phenyl)-6-chloro-4(3H)-quinazolinone ("MAO-HPQ 3") with MAO A. FIG. 2f) shows the fluorescent enhancement of a compound according to one embodiment, 2-(5'-chloro-2 (3-(N,N'-dimethylamino)propoxy)phenyl)-6-chloro-4(3H)-quinazolinone ("MAO-HPQ 3") with MAO B.

FIG. 5a) A bar chart of enzymatic assay of MAO A with HPQ-MAO 1 compared with inhibitor Clorgyline and Pargyline. (b) A bar chart of enzymatic assay of MAO B with HPQ-MAO 1 compared with Clorgyline and Pargyline. (c) Fluorescence detection of enzyme inhibition assays based on PC12 cell lysates. Left: MAO-HPQ 1 incubated PC12 cell lysates; Middle: MAO-HPQ 1 incubated with clorgyline pre-treated PC12 cell lysates; Right: MAO-HPQ 1 incubated with pargyline pre-treated PC12 cell lysates.

FIG. 7 illustrates the HPLC results for the compounds according to various embodiments of the invention with MAO isozymes. Absorbance wavelength: 360 nm.

DETAILED DESCRIPTION OF THE INVENTION

The present invention is based on the surprising finding that the compounds of the invention are able to provide direct and sensitive real-time imaging of enzyme activity in living cell systems. Without wishing to be bound by theory, the imaging of enzyme activity relies on the oxidation of a primary, secondary or tertiary amine in the compounds of the present invention, to produce iminium intermediates, which are further hydrolyzed into the corresponding aldehyde to facilitate the release of a fluorescent product through a β-elimination process (see for example FIG. 1). In this regard, the compounds of the present invention possess unique chemical properties in that they are insoluble in water and fluorescent only in a solid state at the enzyme activity sites, unlike commercially available dyes in which its by-products of the fluorophore substrates are easily diffused and washed away from the site of enzyme activities. Therefore, the compounds of the present invention can rapidly release the fluorescent precipitate with minimum background. The compounds of the present invention are also highly photostable with large stokes shift (more than 100 nm). Thus, the compounds are easily focused and distinguished from most cell and tissue autofluorescence. The compounds are also found to be less toxic (see for example FIG. 6) and more cell permeable without damaging the cellular membrane (see for example FIG. 4).

Figure 1:
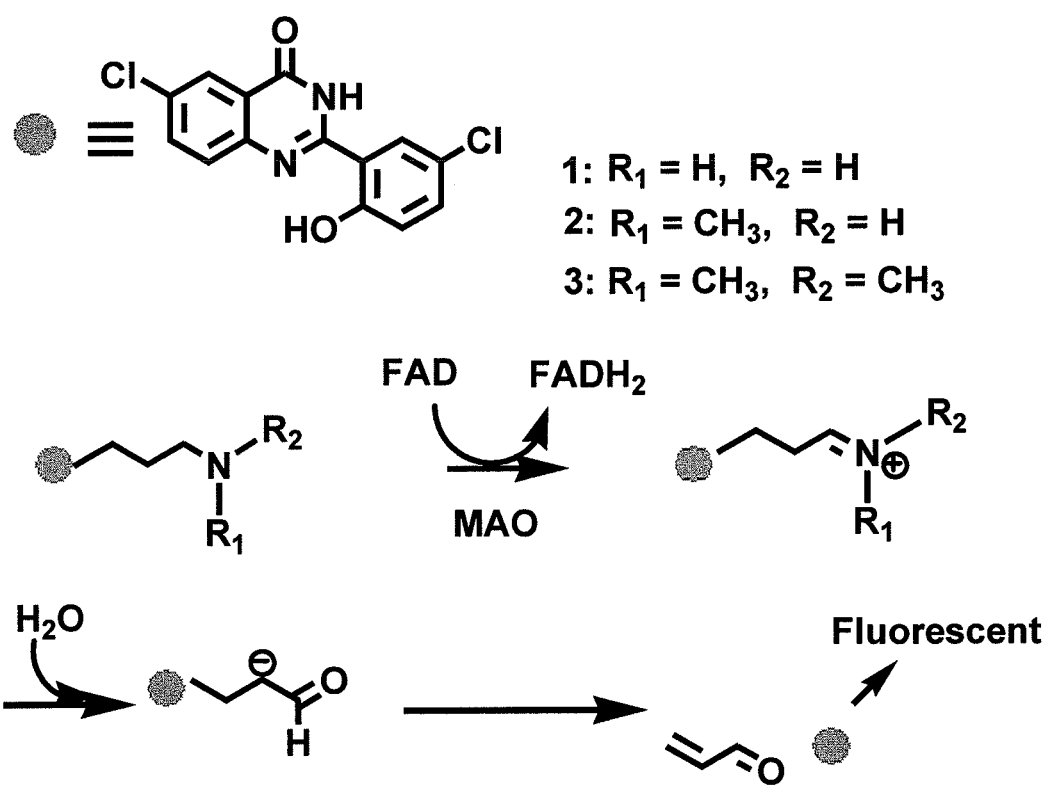
FIG. 1 illustrates the mechanism of oxidative deamination and β-elimination of an enzyme monoamine oxidase (MAO) using the compounds of the invention. The shaded circle represents the compound, 2-(2'-hydroxy-5'-chlorophenyl)-6-chloro-4(3H)-quinazolinone. This compound displays interesting properties towards utilizing optical reporter gene imaging in biochemical assays and cell culture. This enables the monoamine oxidase to release this unique fluorescent precipitates after catabolism by monoamine oxidase by oxidizing the amino group (Primary, Secondary or tertiary) which will immediately undergo a β-elimination to liberate the acrolein and 2-(2'-hydroxy-5'-chlorophenyl)-6-chloro-4(3H)-quinazolinone.

Without wishing to be bound by theory, the alkylation of 2-hydroxyl group in the compound 2-(2'-hydroxy-5'-chlorophenyl)-6-chloro-4(3H)-quinazolinone efficiently eliminates its long wavelength fluorescence, providing an ideal molecular switch to amply the fluorescent signals for enzyme detection in living cells (FIG. 1). Therefore, the compounds of the invention can be used for real-time tracking of the dynamics of cellular function both in vitro and in vivo as described further below.

In a first aspect, the invention thus provides for a compound of general formula

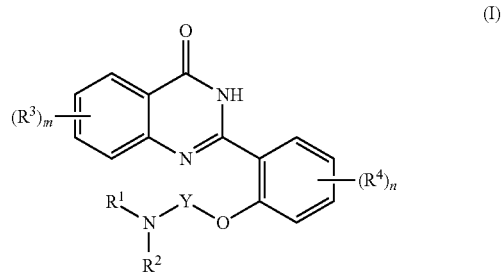

(I)

or a salt, tautomer or stereoisomer thereof.

In this formula, $R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl; each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_5$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O) R, —C(O)OR, —C(O)NRR', —NRR', —S(O)$_2$R, —S(O)$_2$ OR, and —S(O)$_2$NRR'; Y is an aliphatic group; R and R' are independently selected from the group consisting of hydrogen and unsubstituted $C_1$-$C_4$ alkyl; and m and n are integers independently selected from 1, 2, 3 and 4.

The term "aliphatic", alone or in combination, refers to a straight chain or branched chain hydrocarbon comprising at least one carbon atom, and may be saturated or mono- or poly-unsaturated and can include heteroatoms (see below). A saturated aliphatic group has no double or triple bonds. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms. The aliphatic group used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

The term "alkyl", alone or in combination, refers to a fully saturated aliphatic hydrocarbon such as a straight or branched chain hydrocarbon group. The alkyl can be a substituted or unsubstituted alkyl group. In certain embodiments, an alkyl can comprise 1 to 20 carbon atoms, 1 to 15 carbon atoms, 1 to 10 carbon atoms, 1 to 8 carbon atoms, 1 to 6 carbon atoms, or 1 to 3 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means that an alkyl group comprising only 1 carbon atom, or 2 carbon atoms, or 3 carbon atoms, or 4 carbon atoms, or 5 carbon atoms, or 6 carbon atoms, or 7 carbon atoms, or 8 carbon atoms, etc., up to and including 20 carbon atoms. Examples of alkyl groups include, but are not limited to, methyl, ethyl, propyl, n-propyl, isopropyl, butyl, n-butyl, isobutyl, sec-butyl, tert-butyl, tert-amyl, pentyl, hexyl, heptyl, octyl, nonyl, decyl, undecyl, dodecyl, tridecyl, tetradecyl and pentadecyl and the like.

The term "alkenyl" as used herein refers to an alkyl group that contains in the straight or branched hydrocarbon chain one or more double bonds. In certain embodiments, an alkenyl comprises 0 to 10 carbon atoms, for example 2 to 10 carbon atoms, 2 to 8 carbon atoms 2 to 6 carbon atoms or 2 to 4 carbon atoms, wherein a numerical range, such as "2 to 10" or "$C_2$-$C_{10}$", refers to each integer in the given range, e.g. "$C_2$-$C_{10}$ alkenyl" means that an alkenyl group comprising 2 carbon atoms, 3 carbon atoms, etc., up to and including 10 carbon atoms. An alkenyl used in this invention can be an unsubstituted or substituted alkenyl. Examples of alkenyl groups include, but are not limited to, ethenyl, propenyl, butenyl, 1,4-butadienyl, pentenyl, 4-methylhex-1-enyl, 4-ethyl-2-methylhex-1-enyl and the like.

The term "alkenyl" as used herein refers to an alkyl group that contains in the straight or branched hydrocarbon chain one or more double bonds. In certain embodiments, an alkenyl comprises 0 to 10 carbon atoms, 2 to 10 carbon atoms, 2 to 8 carbon atoms, 2 to 5 carbon atoms or 2 to 4 carbon atoms, wherein a numerical range, such as "2 to 10" or "$C_2$-$C_{10}$", refers to each integer in the given range, e.g. "$C_2$-$C_{10}$ alkenyl" means that an alkenyl group comprising 2 carbon atoms, 3 carbon atoms, etc., up to and including 10 carbon atoms. An alkenyl used in this invention can be a substituted or unsubstituted alkenyl. Examples of alkenyl groups include, but are not limited to, ethenyl, propenyl, butenyl, 1,4-butadienyl, pentenyl, 4-methylhex-1-enyl, 4-ethyl-2-methylhex-1-enyl and the like.

The term "alkynyl" as used herein refers to an alkyl group that contains in the straight or branched hydrocarbon chain one or more triple bonds. In certain embodiments, an alkynyl comprises 0 to 10 carbon atoms, for example 2 to 10 carbon atoms, 2 to 8 carbon atoms, 2 to 6 carbon atoms, or 2 to 4 carbon atoms, wherein a numerical range, such as "2 to 10" or "$C_2$-$C_{10}$", refers to each integer in the given range, e.g. "$C_2$-$C_{10}$ alkynyl" means that an alkynyl group comprising 2 carbon atoms, 3 carbon atoms, etc., up to and including 10 carbon atoms. An alkynyl group of this invention may be substituted or unsubstituted. Examples of alkynyl groups include, but are not limited to, ethynyl, propynyl, butynyl, and the like.

The term "alkoxy", alone or in combination, refers to an aliphatic hydrocarbon having an alkyl-O-moiety. An alkoxy can comprises 0 to 10 carbon atoms, for example 1 to 10 carbon atoms, 1 to 8 carbon atoms, 1 to 6 carbon atoms, or 1 to 4 carbon atoms, wherein a numerical range, such as "1 to 10" or "$C_1$-$C_{10}$", refers to each integer in the given range, e.g. "$C_2$-$C_{10}$alkoxy" means that an alkoxy group comprising 1 carbon atom, 3 carbon atoms, etc., up to and including 10 carbon atoms. In certain embodiments, alkoxy groups are optionally substituted. Examples of alkoxy groups include, but are not limited to, methoxy, ethoxy, propoxy, butoxy and the like.

The term "cycloalkyl" refers to a completely saturated hydrocarbon ring. The cycloalkyl group used in this invention may range from $C_3$ to $C_8$. A cycloalkyl group of this invention can for example be optionally substituted. Examples of cycloalkyl groups include, but are not limited to cyclopropyl, cyclobutyl, cyclopentyl, cyclohexyl and the like. Therefore, the term "cycloalkoxy" refers to cycloalkyl-O—, wherein cycloalkyl is defined herein.

The term "aryl" refers to an aromatic ring wherein each of the atoms forming the aromatic ring is a carbon atom. Aryl rings may be formed by five, six, seven, eight, nine, or more than nine carbon atoms. The aryl ring also includes biphenyl ring for example. Aryl groups may be optionally substituted. The term "aromatic" refers to a group comprising a covalently closed planar ring having a delocalized [pi]-electron system comprising 4n+2 [pi] electrons, where n is an integer. Aromatic may be formed by five, six, seven, eight, nine, or more than nine atoms. Aromatics or aryls may be optionally substituted. Examples of aryl or aromatic groups include, but are not limited to phenyl, naphthalenyl, phenanthrenyl, anthracenyl, tetralinyl, fluorenyl, indenyl, and indanyl. The term aromatic also includes, for example, benzenoid groups, connected via one of the ring-forming carbon, atoms, and optionally carrying one or more substituents selected from an aryl, a heteroaryl, a. cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ aminoalkyl, alkylamino, an alkylsulfenyl, an alkylsulfinyl, an alkylsulfonyl, an sulfamoyl, or a trifluoromethyl. In certain embodiments, an aromatic or aryl group is substituted at one or more of the para, meta, and/or ortho positions. Examples of aryl or aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl) phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl, N—($C_1$-$C_6$alkyl)amino substituted aryl or N,N—($C_1$-$C_6$alkyl)amino aryl.

The term "heteroaryl" refers a monocyclic or fused aromatic ring (i.e., rings which share an adjacent pair of atoms) of 5 to 10 ring atoms in which one, two, three or four ring atoms are selected from the group consisting of nitrogen, oxygen and sulfur and the rest being carbon. Heteroaryl rings may be formed by three, four, five, six, seven, eight, nine, or more than nine atoms. Heteroaryl rings may also be fused to at least one ring to form a part of a ring system. The term "ring system" refers to two or more rings, wherein two or more of the rings are fused. The term "fused" refers to structures which two or more rings share one or more bonds. Heteroaryls may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. Examples, without limitation, of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnnolinyl, napthyridinyl, quinolyl, isoquinolyl, tetrazolyl, 5,6,7,8-tetrahydroquinolyl, 5,6,7,8-tetra-hydroisoquinolyl, purinyl, pteridinyl, pyridinyl, pyrimidinyl, carbazolyl, xanthenyl or benzoquinolyl.

The term "substituted" refers to a group in which one, or more than one of the hydrogen atoms has been replaced with one or more group(s) are independently selected from: alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups. Therefore, the term "unsubstituted" means that none of the hydrogen atoms have been replaced.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted or may be fused to one ring to form a ring system. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, 1,3-dioxane, 1,4-dioxin, 1,4-dioxane, piperazine, 1,3-oxathiane, 1,4-oxathiane, tetrahydro-1,4-thiazine, 2H-1,2-oxazine, maleimide, succinimide, barbituric acid, thiobarbituric acid, dioxopiperazine, hydantom, dihydrouracil, morphinone, trioxane, hexahydro-1,3,5-triazine, tetrahydrothiophene, tetrahydrofuran, pyrroline, pyrrolidine, pyridone, pyrrohdione, pyrazone, pyrazolidme, imidazoline, imidazolidine, 1,3-dioxole, 1,3-dioxolane, 1,3-dithiole, 1,3-dithiolane, isoxazoline, isoxazolidine, oxazoline, oxazolidine, oxazolidone, thiazoline, thiazolidine, and 1,3-oxathiolane.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

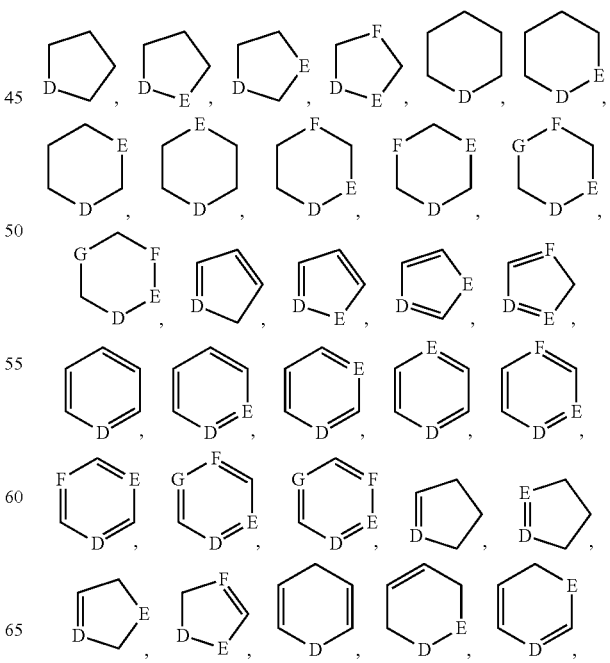

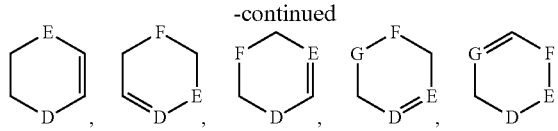

wherein D, E, F, and G independently represents a heteroatom. Each of D, E, F, and G may be the same or different from one another.

A "hydroxy" group refers to an —OH group.

An "aryloxy" group refers to both an —O-aryl and an —O-heteroaryl group, as defined herein. Examples include and are not limited to phenoxy, napthyloxy, pyridyloxy, furanyloxy, and the like.

A "mercapto" group refers to an —SH group.

An "alkylthio" group refers to both an S-alkyl and an —S-cycloalkyl group, as defined herein. Examples include and are not limited to methylthio, ethylthio, and the like.

An "arylthio" group refers to both an —S-aryl and an —S-heteroaryl group, as defined herein. Examples include and are not limited to phenylthio, napthylthio, pyridylthio, furanylthio, and the like.

A "sulfinyl" group refers to a —S(O)—R" group, wherein, R" is selected from the group consisting of hydrogen, hydroxy, alkyl, cycloalkyl, aryl, heteroaryl (bonded through a ring carbon) and heteroalicyclic (bonded through a ring carbon), as defined herein.

A "sulfonyl" group refers to a —S(O)$_2$R" group wherein, R" is selected from the group consisting of hydrogen, hydroxy, alkyl, cycloalkyl, aryl, heteroaryl (bonded through a ring carbon) and heteroalicyclic (bonded through a ring carbon), as defined herein.

"Carbonyl" refers to a —C(=O)—R" group, where R" is selected from the group consisting of hydrogen, alkyl, cycloalkyl, aryl, heteroaryl (bonded through a ring carbon) and heteroalicyclic (bonded through a ring carbon), as defined herein. Representative examples include and the not limited to acetyl, propionyl, benzoyl, formyl, cyclopropylcarbonyl, pyridinylcarbonyl, pyrrolidin-1ylcarbonyl, and the like.

A "thiocarbonyl" group refers to a —C(=S)—R" group, with R" as defined herein.

"C-carboxy" and "carboxy" which are used interchangeably herein refer to a —C(=O)O—R" group, with R" as defined herein, e.g. —COOH, methoxycarbonyl, ethoxycarbonyl, benzyloxycarbonyl, and the like.

An "O-carboxy" group refers to a —OC(=O)R" group, with R" as defined herein, e.g. methylcarbonyloxy, phenylcarbonyloxy, benzylcarbonyloxy, and the like.

An "acetyl" group refers to a —C(=O)CH$_3$ group.

A "halo" or "halogen" group refers to fluorine, chlorine, bromine or iodine.

A "cyano" group refers to a —CN group.

A "nitro" group refers to a —NO$_2$ group.

An "O-carbamyl" group refers to a —OC(=O)NR$^{10}$R$^{11}$ group, with R$^{10}$ and R$^{11}$ as defined herein.

An "N-carbamyl" group refers to a R$^{11}$OC(=O)NR$^{10}$— group, with R$^{10}$ and R$^{11}$ as defined herein.

An "O-thiocarbamyl" group refers to a —OC(=S) NR$^{10}$R$^{11}$ group, with R$^{10}$ and R$^{11}$ as defined herein.

An "N-thiocarbamyl" group refers to a R$^{11}$OC(=S) NR$^{10}$— group, with R$^{10}$ and R$^{11}$ as defined herein.

An "amino" group refers to an —NR$^{10}$R$^{11}$ group, wherein R$^{10}$ and R$^{11}$ are independently hydrogen or unsubstituted lower alkyl, e.g., —NH$_2$, dimethylamino, diethylamino, ethylamino, methylamino, and the like.

A "C-amido" group refers to a —C(=O)NR$^{10}$R$^{11}$ group, with R$^{10}$ and R$^{11}$ as defined herein. For example, R$^{10}$ is hydrogen or unsubstituted C$_1$-C$_4$ alkyl and R$^{11}$ is hydrogen, C$_1$-C$_4$ alkyl optionally substituted with heteroalicyclic, hydroxy, or amino. For example, C(=O)NR$^{10}$R$^{11}$ may be aminocarbonyl, dimethylaminocarbonyl, diethylaminocarbonyl, diethylaminoethylaminocarbonyl, ethylaminoethylaminocarbonyl, and the like.

An "N-amido" group refers to a R$^{11}$C(=O)NR$^{10}$— group, with R$^{10}$ and R$^{11}$ as defined herein, e.g. acetylamino, and the like.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Racemic mixtures can be separated into individual enantiomers by any of a number of conventional methods. These include, but are not limited to, chiral chromatography, derivatization with a chiral auxiliary followed by separation by chromatography or crystallization, and fractional crystallization of diastereomeric salts. Deracemization procedures may also be employed, such as enantiomeric protonation of prochiral intermediate anion, and the like.

The compounds of the invention also include its tautomeric form. The term "tautomer" or "tautomeric form" refers to structural isomers of different energies which are interconvertible via a low energy barrier. For example, protein tautomers (also known as prototropic tautomers) include interconversion via migration of a proton such as keto-enol and imine-enamine isomerizations. Valence tautomers include interconversions by reorganization of some of the bonding electrons.

The compounds disclosed in the invention also include salts or their pharmaceutically acceptable salts. A "pharmaceutically acceptable salt" as used herein, refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences,* 66: 1-19, 1977, which is incorporated herein by reference. Examples of pharmaceutically acceptable, nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, malic acid, 2-hydroxy propanic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, phosphate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

As mentioned above, the compounds disclosed herein also include salts of such compounds which are not necessarily pharmaceutically acceptable salts, and which may be useful as intermediates for preparing and/or purifying compounds of general formula (I) for separating enantiomers of compounds of general formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as malic acid, 2-hydroxy propanic acid, citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

In various embodiments, Y can be a straight or a branched hydrocarbon chain. The hydrocarbon chain can, in some embodiments, be a substituted or unsubstituted $C_1$-$C_{10}$ alkyl as defined herein. In other embodiments, Y can be a substituted or unsubstituted methyl, ethyl, n-propyl, n-butyl, n-pentyl, or n-hexyl, to mention only a few. In a specific embodiment, Y is unsubstituted n-propyl.

In various embodiments, the integers n, m or both are 1. In various embodiments, $R^3$ and $R^4$ or both are independently selected from the group consisting of hydrogen, halogen, unsubstituted or substituted $C_1$-$C_{10}$ alkyl and unsubstituted or substituted $C_1$-$C_{10}$ alkoxy. Within the context of this embodiment, $R^3$, $R^4$, or both are independently halogen. In various embodiments, $R^3$ is in the 6-position of the quinazolinone ring. In various embodiments, $R^4$ is in the 5-position of the phenyl ring. In various embodiments, $R^1$ and $R^2$ are independently selected from the group consisting of hydrogen and unsubstituted or substituted $C_1$-$C_4$ alkyl.

Illustrative examples of a compound of general formula (I) can include, but are not limited 2-(5'-chloro-2'-(3-aminopropoxy)phenyl)-6-chloro-4(3H)-quinazolinone; 2-(5'-chloro-2'-(3-(N-methylamino)propoxy)phenyl)-6-chloro-4(3H)-quinazolinone; and 2-(5'-chloro-2'-(3-(N,N'-dimethylamino)propoxy)phenyl)-6-chloro-4(3H)-quinazolinone.

The invention also provides a method of determining the presence, amount or activity of detecting the activity of a monoamine oxidase. The method includes: i) contacting at least one compound according to the invention with the monoamine oxidase under conditions that allow the oxidative deamination of the compound by the monoamine oxidase; and ii) determining the fluorescence of the compound.

In various embodiments, the presence, amount or activity of a monoamine oxidase can be determined in a biological sample. A "sample" refers to any fluid, solid, jelly, emulsion, slurry or a mixture thereof that contains a membrane compartment. A sample may be an aqueous solution that contains a cell, such as an eukaryotic cell such as a mammalian cell or such as a human cell. The sample may also be a cell for studying the activity of an enzyme. Thus, in some embodiments, the presence, amount or activity of a monoamine oxidase can be determined in a cell, for example a biological cell. A biological cell may be of a mammal, an animal, plant, bacterial or yeast origin. The cells may be living, or dead. The cells may be isolated, in tissue, in vivo or in vitro. Any cells can be used in the method of the invention and include, but not limited to C6 glioma cells, PC12 cells, baby hamster kidney (Bra) cells, mouse L cells, Chinese hamster ovary (CHO) cells, COS-7 cells, blood mononuclear cells (PBMCs), CD4+T cell line, cancer cells, to mention only a few. The methods of the present invention when relating to cells, and samples derived or purified therefrom, including enzyme containing fractions, may be performed in vitro. The methods may, in various embodiments, be performed in vivo.

In various embodiments, the monoamine oxidase can be one of a monoamine oxidase A (MAO A) or monoamine oxidase B (MAO B).

In yet another aspect the invention provides a kit for the detection of the presence or amount of a monoamine oxidase comprising at least one compound described herein. In various embodiments, the kit may comprise one or more components that include instructions for utilizing the at least one compound described herein, for detecting the presence or amount of said monoamine oxidase.

The present invention provides a method of preparing the compound of general formula (I) as described herein including: reacting a compound of general formula (II)

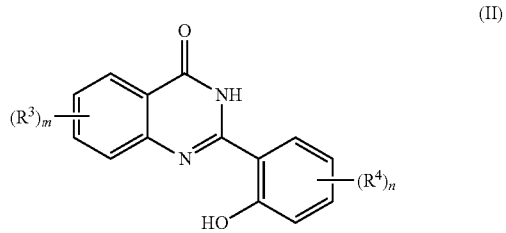

or a salt, tautomer or stereoisomer thereof,
wherein each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_6$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR'; R and R' are independently selected from the group consisting of hydrogen and unsubstituted $C_1$-$C_4$ alkyl; and m and n are integers independently selected from 1, 2, 3 and 4;
with a compound of general formula (III)

(III)

wherein $R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl; Y is an aliphatic group; and X is halogen; in the presence of a base.

Generally, the compounds disclosed herein may be prepared by methods described herein, wherein the substituents are as defined above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In order that the invention may be readily understood and put into practical effect, particular embodiments will now be described by way of the following non-limiting examples.

EXAMPLES

Example 1

Materials and Methods

Materials.
The chemical reagents were purchased from Aldrich or Fluka. Monoamine Oxidase A and B (5 mg/ml) were purchased from Sigma Aldrich. MAO A inhibitor: Clorgyline and MAO B inhibitor: Pargyline was purchased from Sigma. Commercially available reagents were used without further purification, unless noted otherwise. Anhydrous solvents for organic synthesis were purchased from Aldrich and stored over activated molecular sieves (4 Å). Thin-layer chromatography (TLC) was performed on precoated silica gel 60E-254 glass plates.

Instruments.
NMR spectra were recorded on Bruker 300 MHz spectrometer. Mass spectra (MS) were measured with a Thermo Polaris Q for EI and Thermo LCQ Deca XP MAX for ESI. Fluorescence spectroscopic studies were performed on a Varian Cary eclipse Fluorescence spectrophotometer. RP-HPLC analysis was performed on a reverse-phase column with a Shimadzu HPLC system.

Example 2

Synthesis & Characterization of MAO-HPQ 1, 2, 3

Scheme 1: Synthetic route for enzyme substrates MAO-HPQ 1, 2, 3. Boc stands for tert-butoxycarbonyl group.

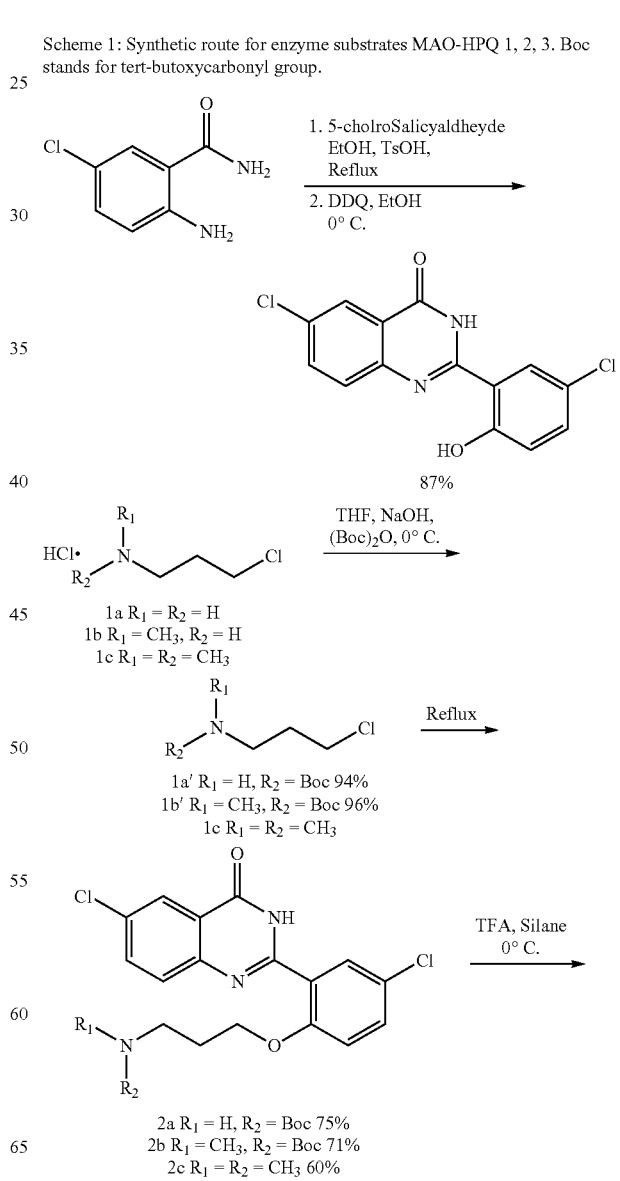

-continued

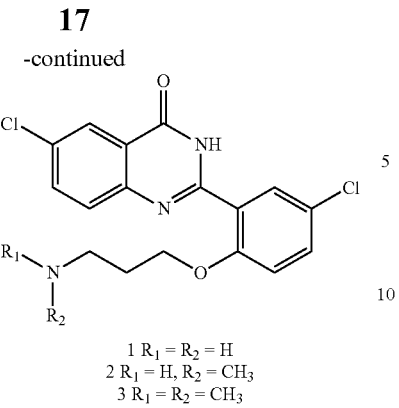

1 R₁ = R₂ = H
2 R₁ = H, R₂ = CH₃
3 R₁ = R₂ = CH₃

Scheme 1 shows the synthesis of MAO-HPQ fluorescent substrates according to various embodiments of the present invention. The preparation of the substrates was divided into two sections: firstly, 2-(2'-hydroxy-5'-chlorophenyl)-6-chloro-4(3H)-quinazolinone fluorophore was synthesized by refluxing 2-amino-5-chlorobenzamide and 5-chlorosalicylaldehyde in ethanol in the presence of catalytic amount of TsOH.H₂O followed by in situ oxidation with dichloro-dicyanoquinone (DDQ). The fluorophore was then alkylated with N,N-dimethyl-3-chloropropylamine using cesium carbonate as base to afford MAO-HPQ 3 in 60% yield. These alkylation conditions were also applied for the synthesis of N-Boc-protected precursors of other two probes, 1b and 2b (yield: 75% and 71%), respectively, which were further deprotected using TFA and triisopropylsilane to give MAO-HPQ 1 and 2 quantitatively.

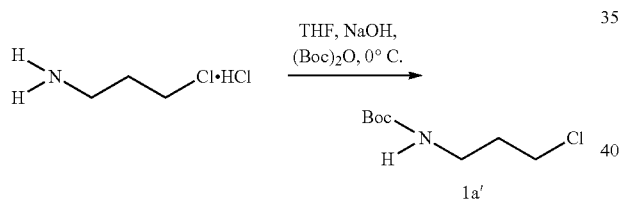

1a'

Preparation of Compound 1a

Di-tert-butyl-dicarbonate (0.228 g, 1.04 mmol) and sodium hydroxide (0.096 g, 2.4 mmol) were added to a cooled solution of 3-chloropropan-1-amine (0.15 g, 1.04 mmol) in water (10 ml) and THF (10 ml). The resulting mixture was stirred overnight at 0° C. The aqueous layer was then extracted with ethyl acetate (10 ml×4). The combined organic layer was washed with brine (25 ml), dried over sodium sulfate and concentrated. The residue was then purified by column chromatography on silica gel to afford 0.306 g of colorless oil. Yield: 94.0%. ¹H NMR (300 MHz, CDCl₃) δ1.39 (s, 9H), δ1.91 (m, 2H), δ3.23 (m, 2H), δ3.53 (t, J=6.4 Hz, 2H), δ4.89 (s, 1H). ¹³C NMR (75 MHz, CDCl₃) δ (ppm): 156.0, 79.2, 42.3, 37.9, 32.6, 28.3. MS (ESI): m/z calcd for C₈H₁₆ClNO₂ 193.09. found 193.52 [M+H]⁺

-continued

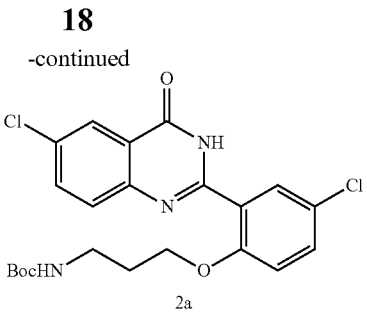

2a

Preparation of Compound 2a is according to the preparation of 1a. Colorless oil, yield: 96.0%. ¹H NMR (300 MHz, CDCl₃) δ1.37 (s, 9H), δ1.91 (m, 2H), δ2.78 (s, 3H), δ3.27 (t, J=6.5 Hz, 2H), δ3.46 (t, J=6.5 Hz, 2H). ¹³C NMR (75 MHz, CDCl₃) δ (ppm): 155.6, 79.4, 46.2, 42.2, 34.4, 30.9, 28.3. MS (ESI): m/z calcd for C₉H₁₈ClNO₂ 207.1. found 207.56 [M+H]⁺

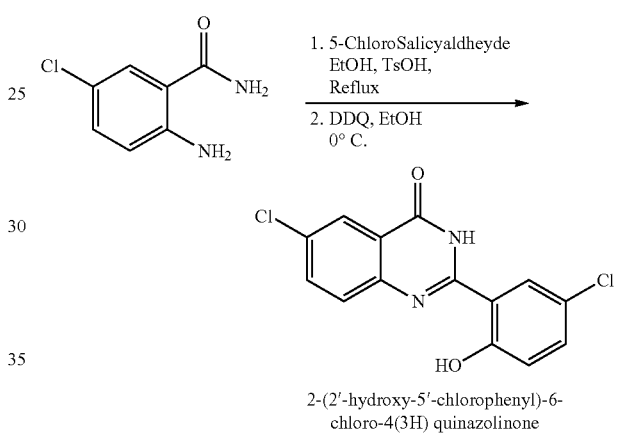

2-(2'-hydroxy-5'-chlorophenyl)-6-chloro-4(3H) quinazolinone

Preparation of 2-(2'-hydroxy-5'-chlorophenyl)-6-chloro-4(3H)-quinazolinone

In a 25 ml three-necked flask, a mixture of 4-chloroanthranilamide (0.170 g, 1.0 mmol), 5-chlorosalicydehyde (0.156 g, 1.0 mmol) and TsOH.H₂O (18.0 mg, 0.1 mmol) were dissolved in 10 ml of anhydrous ethanol and heated at reflux for 1 hour. The reaction mixture was then cooled to 0° C. and 2,3-dichloro-4,5-dicyano-1,4-benzoquinone (0.228 g, 1.0 mmol) was added. The resultant suspension was stirred at 0° C. for another 1 hour and a greenish precipitate was formed. The solid was collected by filtration and washed with a small amount of cooled ethanol to afford 0.301 g of the desired greenish-white compound. Yield: 86.0%. ¹H NMR (300 MHz, DMSO-d₆), δ8.29 (d, J=2.2 Hz, 1H), δ8.10 (d, J=2.1 Hz, 1H), δ7.83-7.92 (m, 2H), δ7.49 (dd, J=2.5, 8.9 Hz, 1H), δ7.05 (d, J=8.8 Hz, 1H) ¹³C NMR (75 MHz, DMSO-d₆) δ (ppm): 135.7, 134.0, 132.0, 129.9, 129.3, 127.8, 125.8, 123.0, 121.8, 120.0, 116.3.

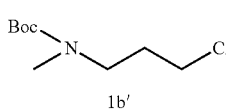

1b'

Preparation of Compound 1b

A mixture of 2-(2'-hydroxy-5'-chlorophenyl)-6-chloro-4(3H)-quinazolinone (0.1 g, 0.33 mmol) and 1a were dissolved in 3 ml of DMF. Cesium carbonate (0.429 g, 1.32 mmol) was added in and the mixture was stirred at reflux overnight. After the reaction was finished, the mixture was poured in 15 ml water and extracted with ethyl acetate (20 ml×3). The combined organic layer was washed with brine (30 ml), dried over $Na_2SO_4$ and concentrated. The yellow-orange residue was then purified with flash chromatography with eluent ethyl acetate and hexane (1:1) to afford 0.113 g product as yellow solid. Yield: 75.2%. $^1$H NMR (300 MHz, DMSO-d$_6$), δ8.08 (d, J=2.4 Hz, 1H), δ7.88 (dd, J=2.4, 8.7 Hz, 1H), δ7.76 (d, J=8.7 Hz, 1H), δ7.71 (d, J=2.7 Hz, 1H), δ7.58 (dd, J=2.7, 8.9 Hz, 1H), δ7.22 (d, J=8.9 Hz, 1H), δ6.90 (t, J=5.5 Hz, 1H), δ4.06 (t, J=5.8 Hz, 2H), δ3.05-3.11 (m, 2H), δ1.80 (m, 2H), δ1.32 (s, 9H). $^{13}$C NMR (75 MHz, DMSO-d$_6$) δ (ppm): 160.6, 155.9, 151.9, 148.1, 135.0, 131.6, 130.2, 125.3, 124.6, 122.8, 115.2, 92.8, 78.1, 66.4, 36.7, 29.7, 28.7. MS (ESI): m/z calcd for $C_{22}H_{23}Cl_2N_3O_4$ 463.11. found 463.91 [M+H]$^+$

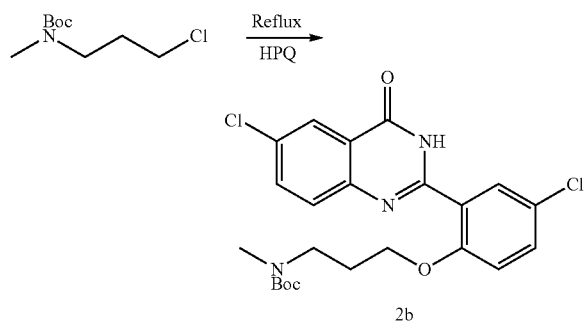

Preparation of Compound 2b

Prepared in a similar way as 1b. 0.112 g of yellow precipitate was obtained. Yield: 71.0%. $^1$H NMR (300 MHz, CDCl$_3$) δ8.25 (d, J=1.5 Hz, 1H), δ8.10 (s, 1H), δ7.68-7.74 (m, 21-1H), δ7.40 (d, J=8.5 Hz, 1H), δ6.91 (d, J=8.5 Hz, 1H), δ4.04 (t, J=6.6 Hz, 2H), δ3.61 (t, J=8.1 Hz, 2H), δ2.90 (s, 3H), δ2.09-2.13 (m, 2H), δ1.32 (s, 9H), $^{13}$C NMR (75 MHz, CDCl$_3$) δ (ppm): 161.0, 156.2, 155.5, 150.9, 147.8, 134.7, 132.4, 132.2, 130.9, 129.4, 126.5, 125.8, 122.8, 122.6, 113.4, 79.9, 65.5, 44.5, 34.2, 28.2, 26.7. MS (ESI) m/z calcd for $C_{23}H_{25}Cl_2N_3O_4$ 477.12. found 477.72 [M+H]$^+$

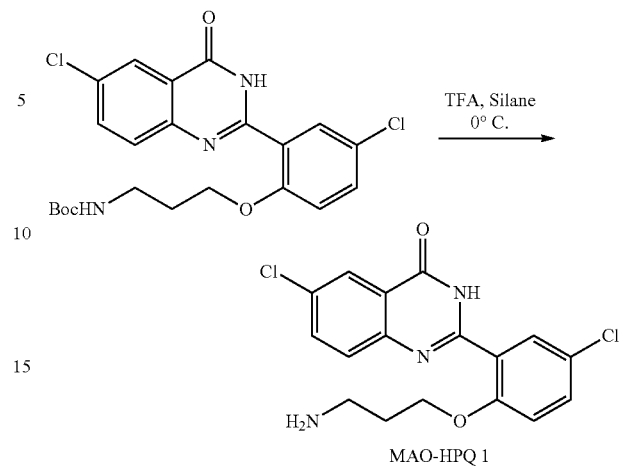

MAO-HPQ 1

Preparation of MAO-HPQ 1 (2-(5'-chloro-2'-(3-aminopropoxy)phenyl)-6-chloro-4(3H)-quinazolinone)

Compound 2a (0.113 g, 0.0244 mmol) was dissolved in 500 μl of trifluoroacetic acid and followed by an addition of 20 μl of triisopropylsilane. The mixture was stirred in an ice-bath for 1 hr under $N_2$ atmosphere. The solvent was removed by concentration and the residue was washed with cold ether (3×3 ml) to afford 88.6 mg greenish precipitate. Yield: 98.2%. $^1$H NMR (300 MHz, DMSO-d$_6$) δ8.09 (d, J=2.4 Hz, 1H), δ7.86-7.89 (m, 2H), δ7.76 (d, J=8.7 Hz, 1H), δ7.68 (d, J=2.7 Hz, 1H), δ7.60 (dd, J=2.7, 8.7 Hz, 1H), δ7.22 (d, J=8.8 Hz, 1H), δ4.16 (t, J=6.3 Hz, 2H), δ2.91-2.97 (m, 2H), δ1.95-2.03 (m, 2H), $^{13}$C NMR (75 MHz, DMSO-d$_6$) δ (ppm): 155.5, 152.0, 135.0, 132.2, 131.6, 130.4, 130.2, 125.3, 124.8, 122.9, 115.0, 70.7, 66.0, 36.7, 27.1. MS (ESI): m/z calcd for $C_{17}H_{15}Cl_2N_3O_2$ 363.05. found 364.00 [M+H]$^+$

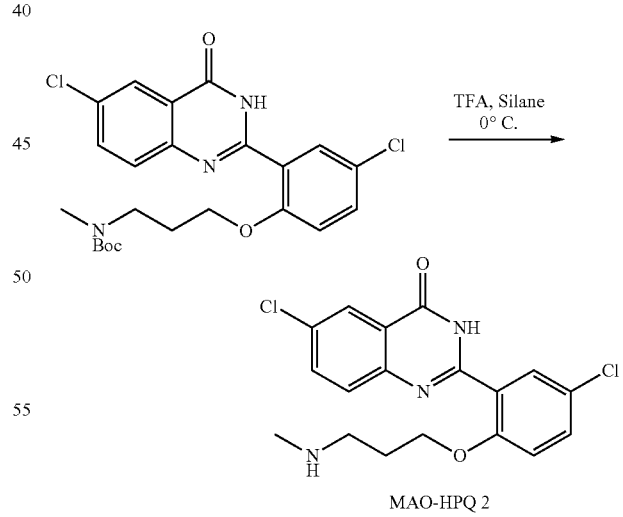

MAO-HPQ 2

Preparation of MAO-HPQ 2 (2-(5'-chloro-2'-(3-(N-methylamino)propoxy)phenyl)-6-chloro-4(3H)-quinazolinone)

Prepared in a similar manner as MAO-HPQ 1. The final product obtained was 34.6 mg. Yield: 89.0%. NMR (300

MHz, DMSO) δ8.57 (s, 1H), δ8.10 (d, J=1.6 Hz, 1H), δ7.89 (dd, J=2.2, 9.0 Hz, 1H), δ7.77 (d, J=8.5 Hz, 1H), δ7.68 (d, J=2.9 Hz, 1H), δ7.59 (dd, J=2.8, 8.5 Hz, 1H), δ7.23 (d, J=8.5 Hz, 1H), δ4.15 (m, 2H), δ3.00-3.08 (m, 2H), δ2.57 (s, 3H), δ2.04 (m, 2H) $^{13}$C NMR (75 MHz, DMSO-$d_6$) δ (ppm): 160.8, 158.7, 155.5, 152.0, 148.0, 135.1, 132.2, 131.6, 130.3, 130.1, 125.3, 124.9, 124.7, 122.9, 115.0, 70.7, 65.7, 46.1, 33.1, 25.7. MS (ESI): m/z calcd for $C_{18}H_{17}Cl_2N_3O_2$ 377.07. found 378.01[M+H]$^+$

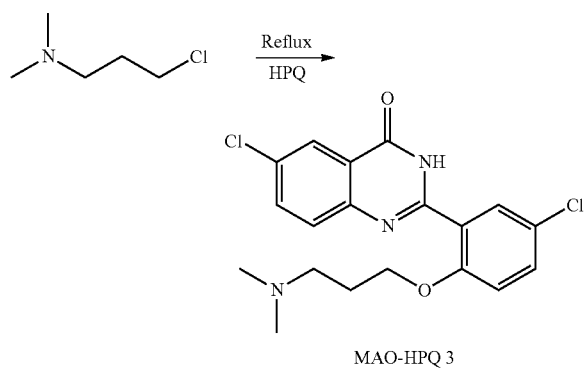

Preparation of Substrate MAO-HPQ 3 (2-(5'-chloro-2'-(3-(N,N'-dimethylamino)propoxy)phenyl)-6-chloro-4(3H)-quinazolinone)

Prepared in a similar manner as 1b. A yellow-orange precipitate was obtained as the final product with a total yield of 0.078 mg (60.1%). $^1$HNMR (300 MHz, DMSO-$d_6$), δ8.29 (d, J=2.6 Hz, 1H), δ8.09 (d, J=2.2 Hz, 1H), δ7.82-7.91 (m, 2H), δ7.49 (dd, J=2.6, 8.8 Hz, 1H), δ7.04 (d, J=8.8 Hz, 1H), δ3.73 (t, J=6.3 Hz, 2H), δ3.13 (t, J=7.9 Hz, 2H), δ2.75 (s, 6H), δ 2.08-2.17 (m, 2H). $^{13}$C NMR (75 MHz, DMSO-$d_6$) δ (ppm): 180.8, 165.9, 165.1, 164.7, 160.4, 149.4, 132.7, 131.6, 128.5, 127.6, 127.5, 125.3, 123.1, 121.1, 119.8, 70.7, 56.5, 19.0. MS (ESI): m/z calcd for $C_{19}H_{19}Cl_2N_3O$ 391.09. found 392.08 [M+H]$^+$ Example 3

Enzymatic Assays

Enzymatic Activity of MAO Substrates

Activity of fluorogenic MAO-HPQ 1, 2 and 3 were determined by the fluorescence intensity after incubations separately with monoamine oxidase A or B at 37° C. for 2 hours. Typically, 5 µl of MAO A and B enzyme solution (final concentration of 10 µg/ml) was incubated with MAO substrates 1, 2 and 3 (final concentration of 200 µM) in a 100 mM Tris-HCl buffer, pH 7.90, 5% glycerol and 5% DMSO. After 2 hours of incubation, the fluorescent enhancement was monitored by Fluorescence spectrophotometer with excitation wavelength at 360 nm.

Figure 2:
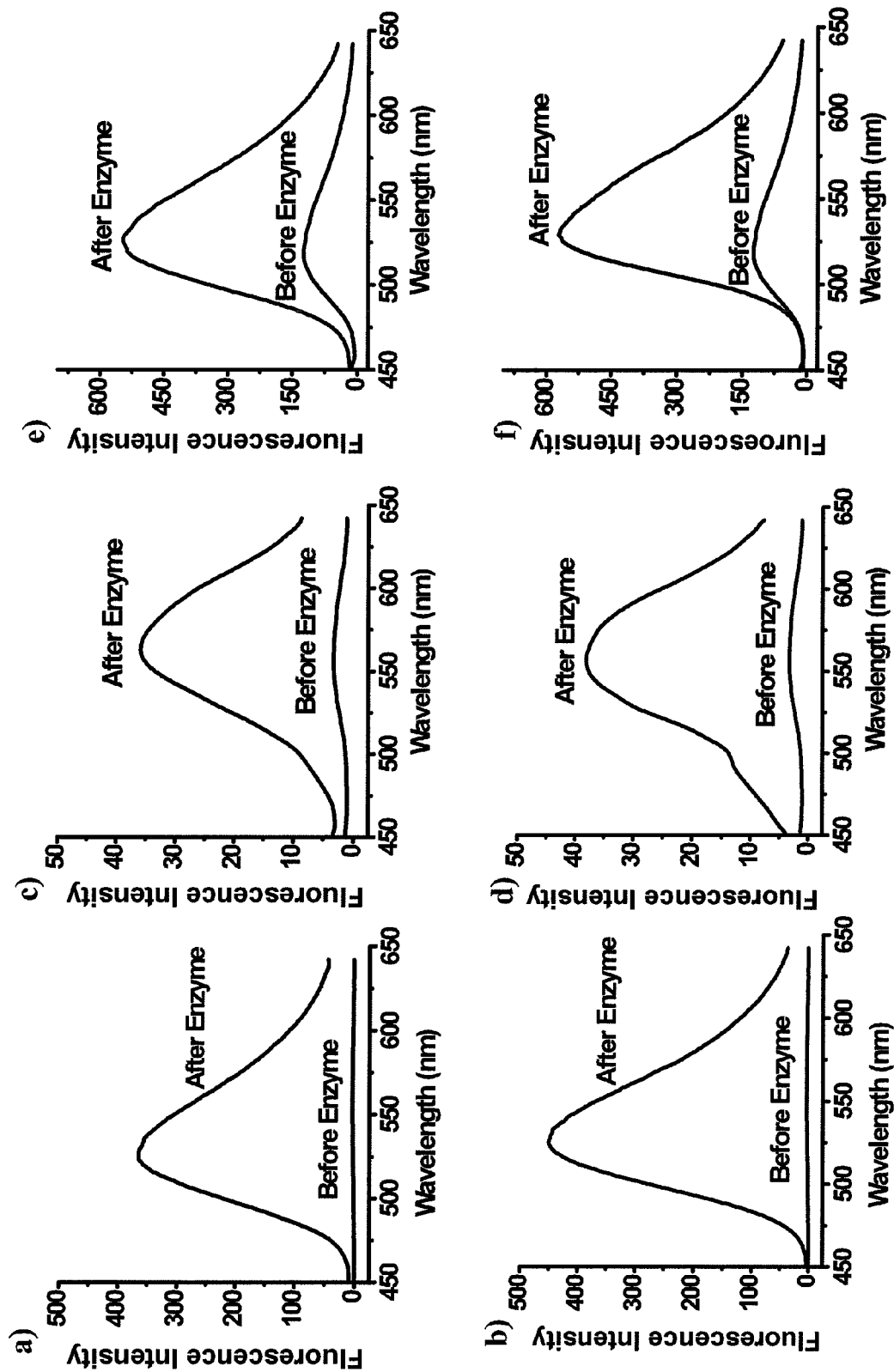
FIG. 2 depicts the fluorescent measurements of MAO enzymatic reactions upon treatment with compounds according to various embodiments of the invention.
Figure 3:
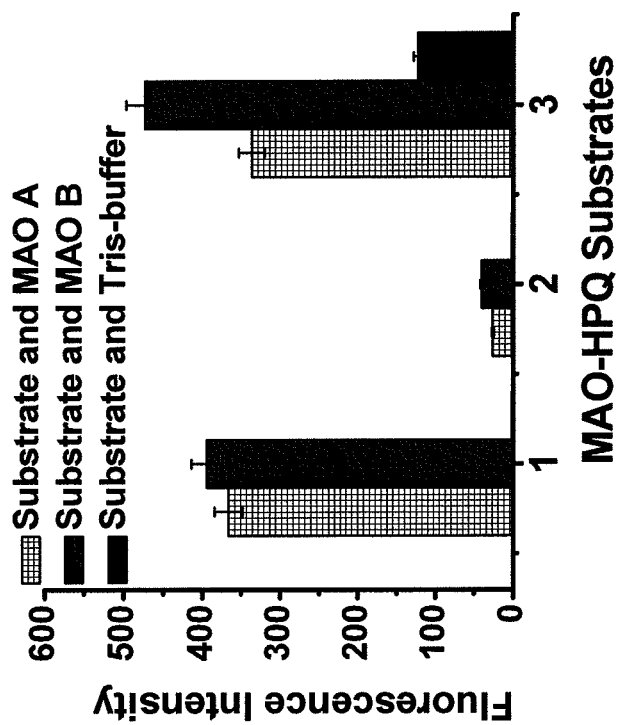
FIG. 3a) illustrates a representative enzymatic kinetics plot of 2-(5'-chloro-2'-(3-aminopropoxy)phenyl)-6-chloro-4(3H)-quinazolinone (MAO-HPQ 1) with both MAO A and MAO B according to an embodiment of the present invention. Data shows a relative reaction rates over a range of concentrations of the substrate MAO-HPQ 1. These values were obtained with an average of at least 6 independent experiments for each concentration and collected over a time frame of 60 minutes.
FIG. 3(b) illustrates the fluorescence increment of MAO-HPQ substrates namely MAO-HPQ 1 (2-(5'-chloro-2'-(3-aminopropoxy)phenyl)-6-chloro-4(3H)-quinazolinone), MAO-HPQ 2 (2-(5'-chloro-2'-(3-(N-methylamino)propoxy) phenyl)-6-chloro-4(3H)-quinazolinone) and MAO-HPQ 3 (2-(5'-chloro-2'-(3-(N,N'-dimethylamino)propoxy)phenyl)-6-chloro-4(3H)-quinazolinone) (200 µM) when contacted with MAO A, MAO B or Tris buffer.
Figure 3:
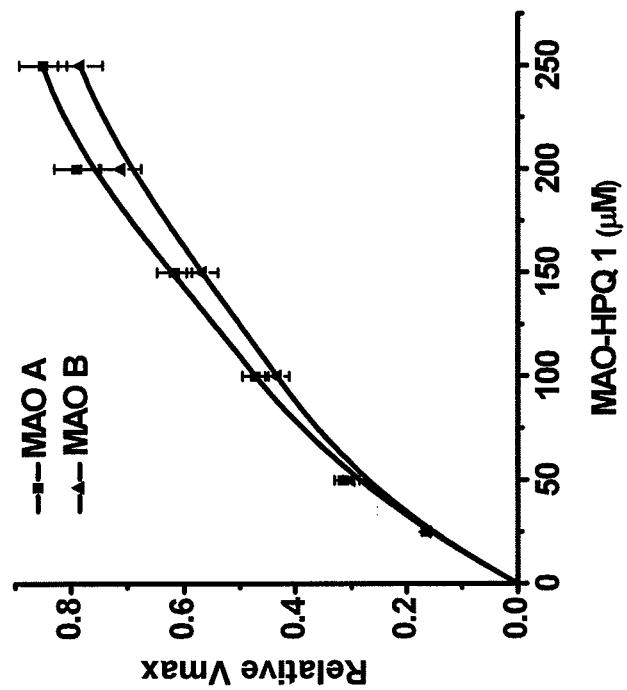

The activity of these three probes (MAO-HPQ 1~3) towards both MAO isozymes were investigated by in vitro fluorescent measurements. All the MAO substrates 1, 2, and 3 were very stable in aqueous solutions and were almost nonfluorescent before MAO enzymatic oxidation due to the alkylation of the 2'-hydroxyl group in the 2-(2'-hydroxy-5'-chlorophenyl)-6-chloro-4(3H)-quinazolinone fluorophore. However, upon treatment with MAO A and B, 2-(2'-hydroxy-5'-chlorophenyl)-6-chloro-4(3H)-quinazolinone molecules were released and significant fluorescence enhancement around the wavelength of 530 nm was observed in all substrates (FIGS. 2 and 3b).

Example 4

HPLC Analysis

The enzymatic oxidations of fluorogenic substrates MAO-HPQ 1, 2 and 3 were confirmed with analytical reverse-phase high performance liquid chromatography. RP-HPLC was performed on Alltima C-18 column (250×3.0 mm) at a flow rate of 1.0 ml/min. An eluting system consisting of A (water with 0.1% TFA) and B (acetonitrile with 0.1% TFA) was used under a linear gradient to elute the products, which was monitored by UV-Visible absorbance at 360 nm. The linear gradient started from 80% solution A and 20% solution B, changed to 20% solution A and 80% solution B in 30 minute and to 0% solution A and 100% solution B in the following 5 minutes, and then back to 80% solution A and 20% solution B in the next 5 minutes.

Figure 7A:
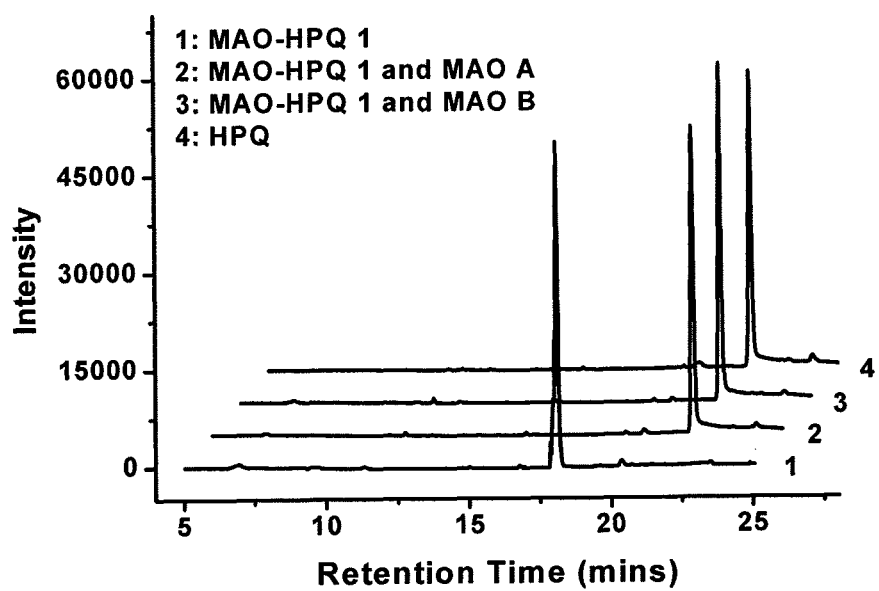
FIG. 7a) HPLC results for substrate MAO-HPQ 1 (2-(5'-chloro-2'-(3-aminopropoxy)phenyl)-6-chloro-4(3H)-quinazolinone) with MAO A and B.
Figure 7B:
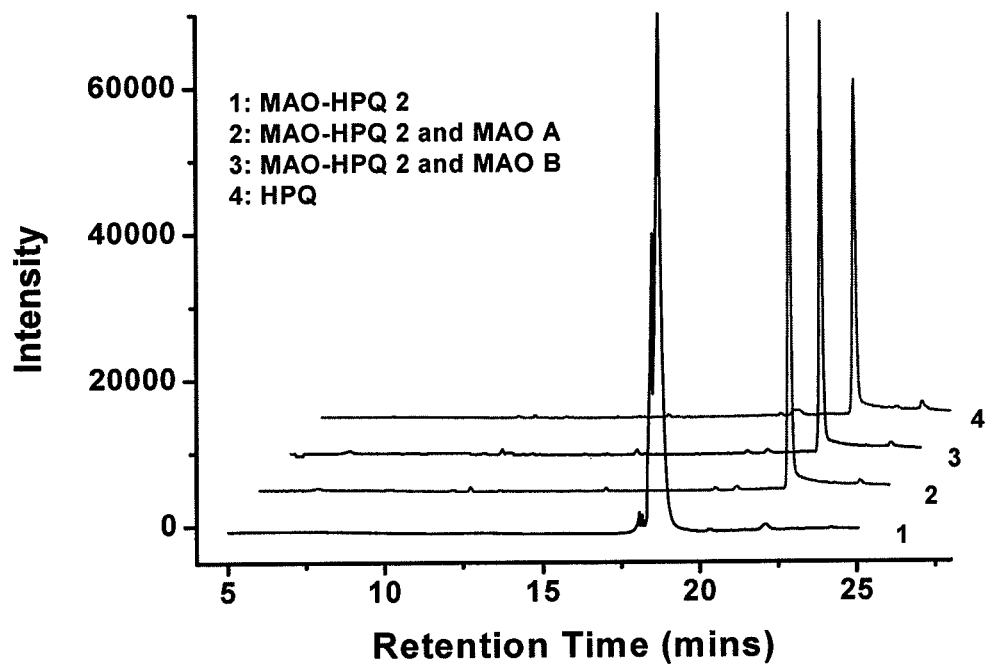
FIG. 7b) HPLC results for substrate MAO-HPQ 2 (2-(5'-chloro-2'-(3-(N-methylamino)propoxy)phenyl)-6-chloro-4(3H)-quinazolinone) with MAO A and B.
Figure 7C:
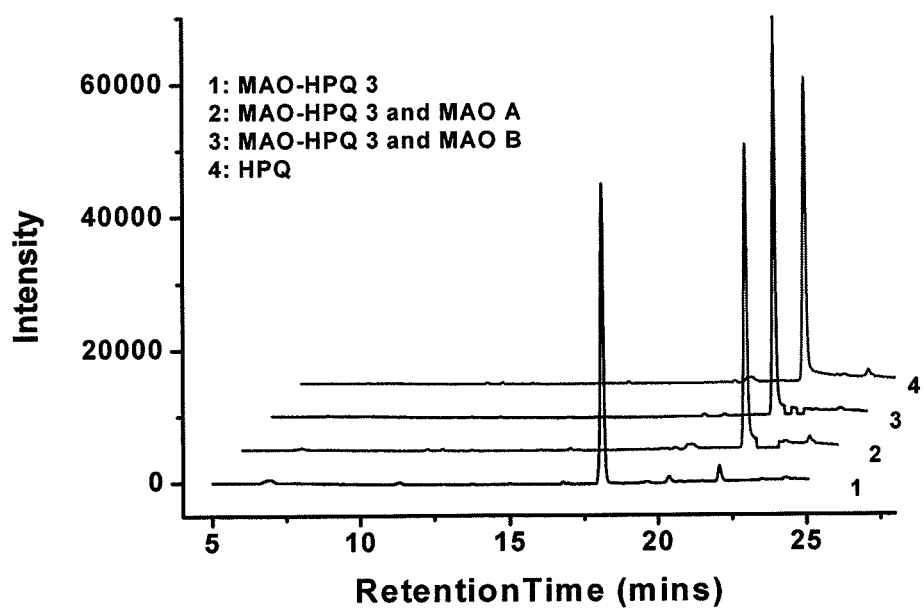
FIG. 7c) HPLC results for substrate MAO-HPQ 3 (2-(5'-chloro-2'-(3-(N,N'-dimethylamino)propoxy)phenyl)-6-chloro-4(3H)-quinazolinone) with MAO A and B. "HPQ" represents 2-(2'-hydroxy-5'-chlorophenyl)-6-chloro-4(3H)-quinazolinone.
Figure 8A:
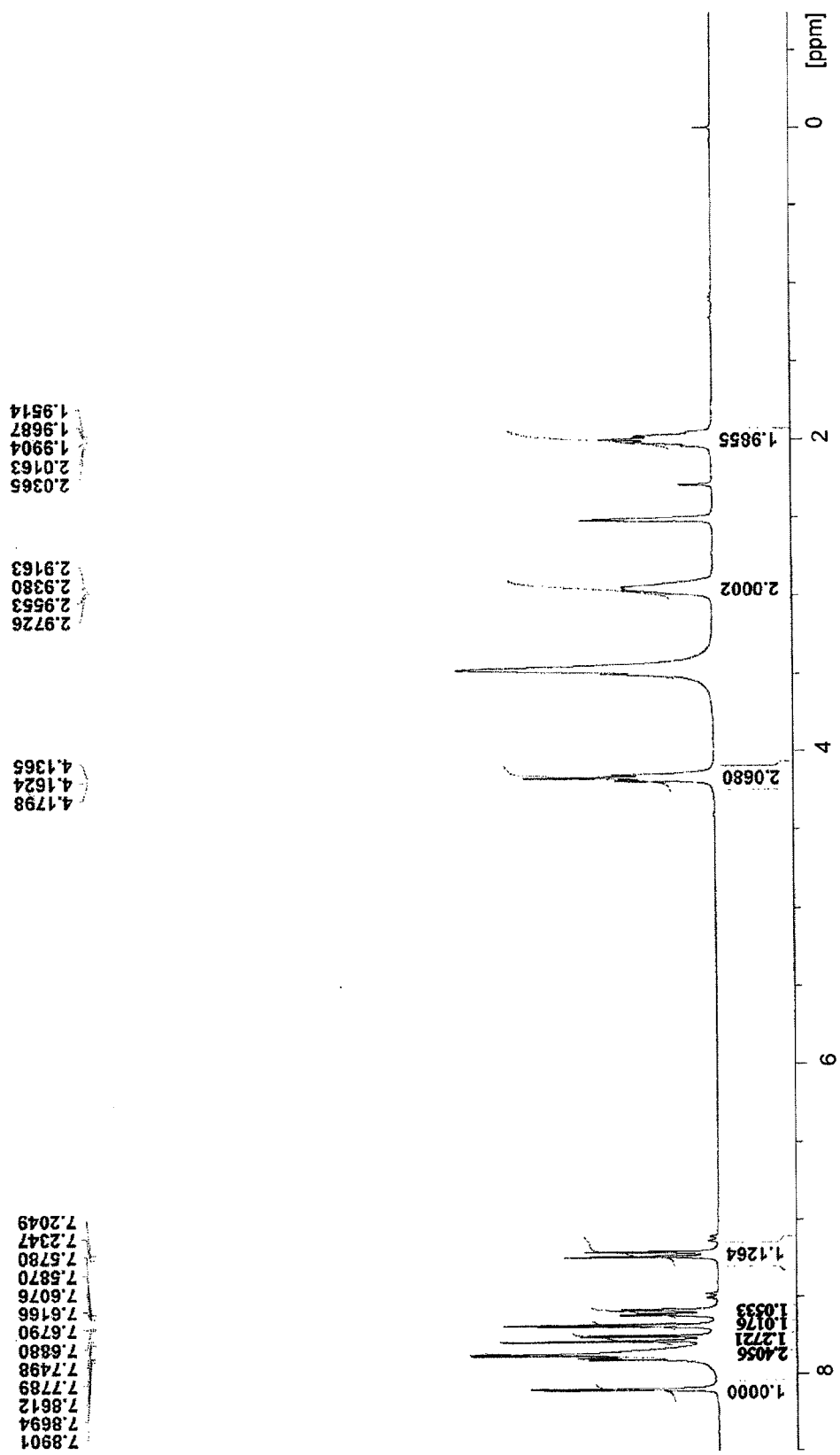
FIG. 8a) to c) depict the NMR spectra of the compounds according to various embodiments of the invention namely, MAO-HPQ 1, MAO-HPQ 2 and MAO-HPQ 3 respectively.
Figure 8B:
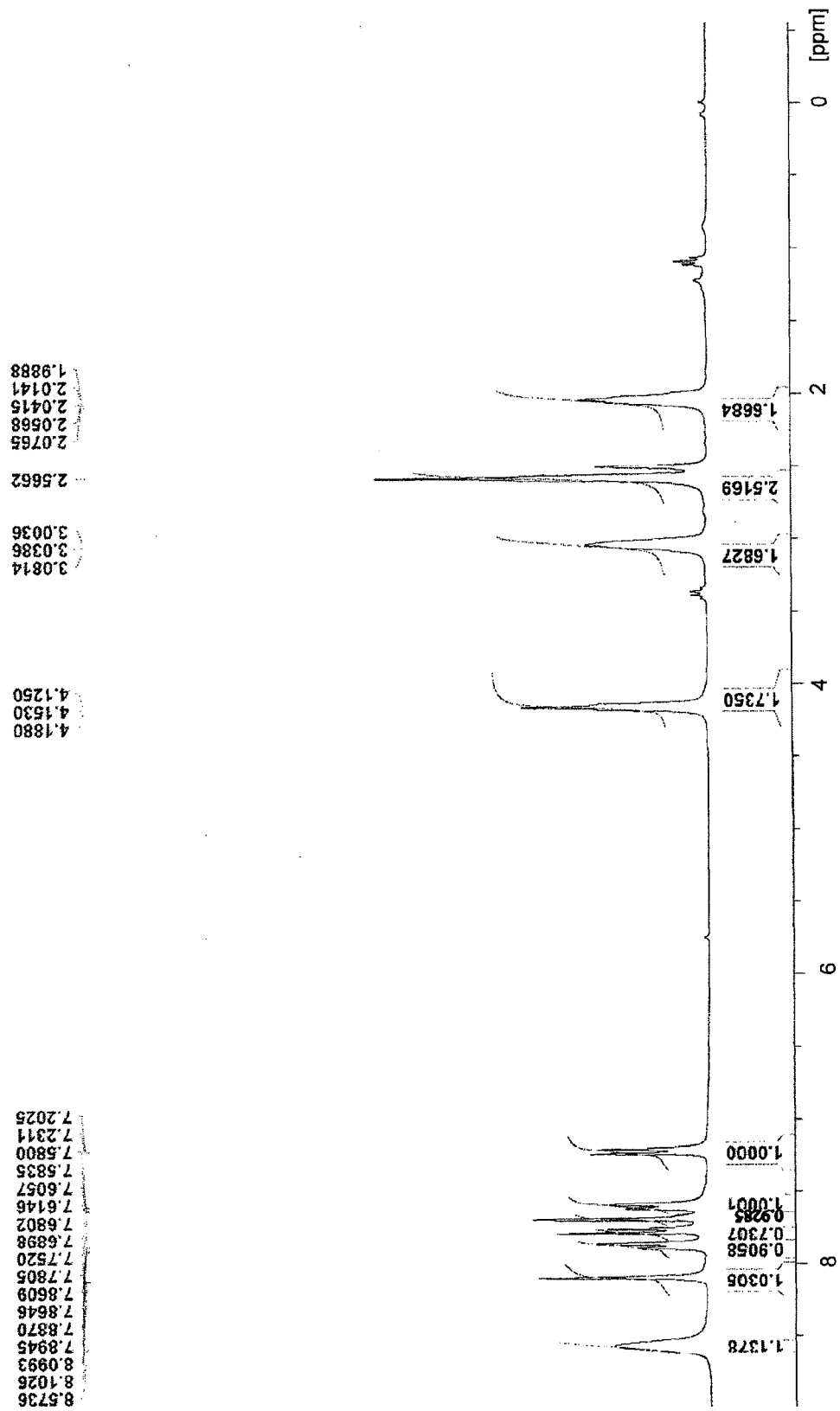
Figure 8C:
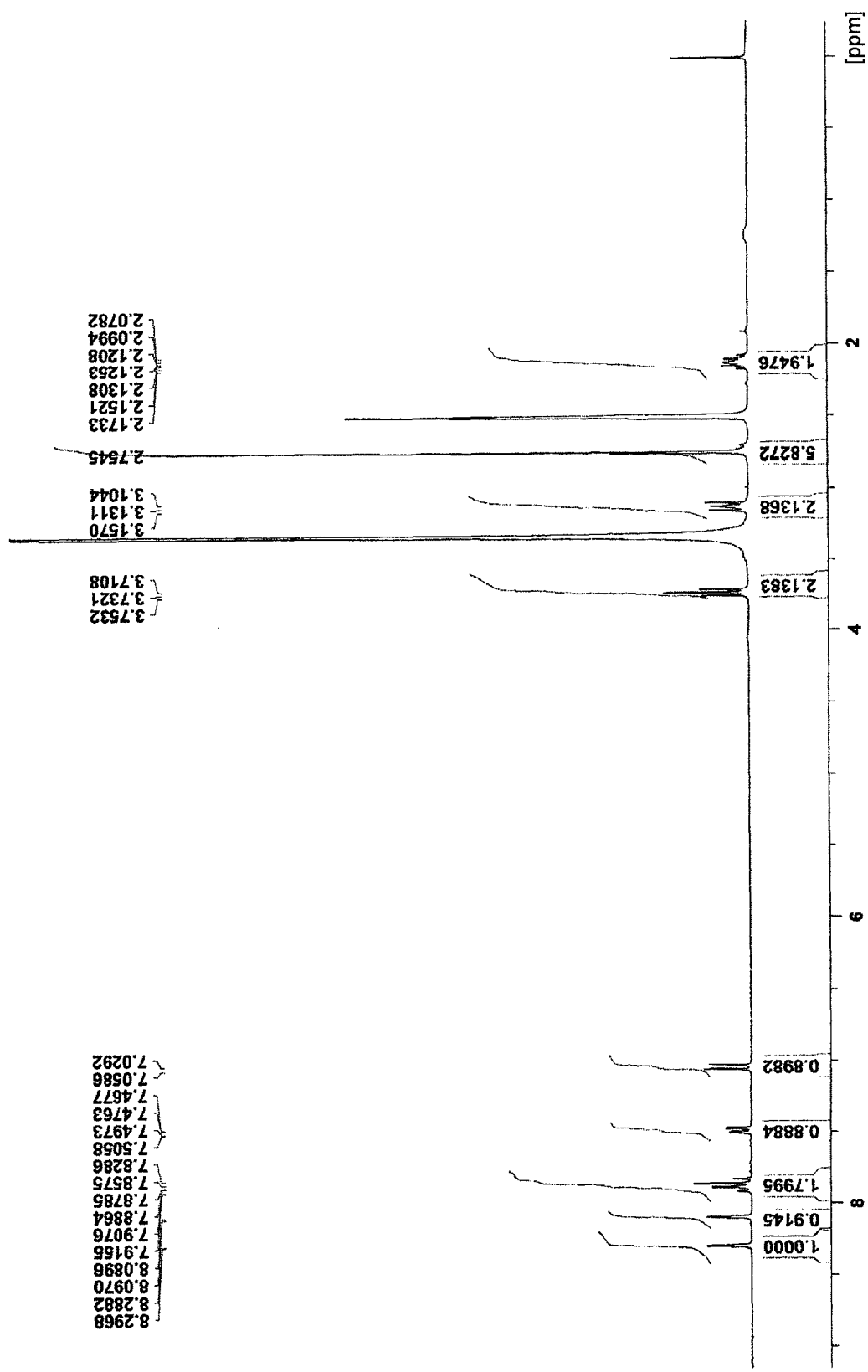

The formation of 2-(2'-hydroxy-5'-chlorophenyl)-6-chloro-4(3H)-quinazolinone fluorophore in the enzymatic reactions was further confirmed by HPLC analysis. In the presence of each MAO isozyme, the retention time of enzymatic product was same as that of 2-(2'-hydroxy-5'-chlorophenyl)-6-chloro-4(3H)-quinazolinone (retention time: 21.8 min), approving the enzyme-mediated reactions to release 2-(2'-hydroxy-5'-chlorophenyl)-6-chloro-4(3H)-quinazolinone fluorophores from all the substrates (FIG. 7).

Fluorescent enhancement and HPLC results confirmed that all the primary, secondary and tertiary MAO-HPQ fluorescent substrates underwent an oxidative deamination catalyzed by MAO enzymes, followed by β-elimination, which resulted in the release of 2-(2'-hydroxy-5'-chlorophenyl)-6-chloro-4(3H)-quinazolinone fluorescent precipitates. The ratio of fluorescent intensity in the presence and absence of MAO enzymes were used to estimate MAO activities. The maximum fluorescent enhancement in the primary, secondary and tertiary amine MAO substrates was 307-fold, 15-fold, and 5-fold for MAO A and 300-fold, 20-fold and 7-fold for MAO B, respectively (FIG. 3b), indicating that the different amine substrates exhibited different activities toward MAO enzymes. Of the three MAO-HPQ derivatives, substrate 1 exhibited an intensive fluorescence signal and the highest signal-to-background ratio at 530 nm, affording a convenient means with which to measure MAO activity.

Example 5

Enzymatic Kinetics of MAO-HPQ 1

The enzyme kinetics was carried out in Tris-buffer (100 mM, pH 7.90) at 25° C. The enzymatic oxidation of fluorogenic substrate MAO-HPQ 1 was monitored in Varian Cary eclipse Fluorescence spectrophotometer. To a series of different MAO-HPQ 1 substrate concentration (ranged from 0~250 µM) were added a solution of MAO A or MAO B enzyme with final concentration of 5 Tris-buffer was added to adjust the final volume to 100 µl. The rate of enzymatic oxidation was monitored with the increase of fluorescent enhancement at 530 nm. The values of the enzyme kinetic parameters ($K_m$ and $K_{cat}$) were determined from the standard Lineweaver-Burk plot, the double-reciprocal plot of the reaction rate versus MAO-HPQ 1 concentration.

FIG. 3a shows a representative enzyme kinetics plot of MAO-HPQ 1 for MAO A and B oxidation. Measurement of the fluorescent signal at different substrate concentrations provided the Michaelis-Menten kinetics constants. These observed kinetic parameters were determined to be: $K_m=146.1\pm7.21$ μM, $K_{cat}=9.76\pm0.49$ min$^{-1}$ for MAO A and $K_m=106.8\pm5.06$ μM, $K_{cat}=8.47\pm0.42$ min$^{-1}$ for MAO B. The enzyme catalytic efficiency ($K_{cat}/K_m$) for MAO A and B are $6.68\times10^4$ M$^{-1}$ min and $7.93\times10^4$ M$^{-1}$ min$^{-1}$, respectively.

Example 6

Figure 6:
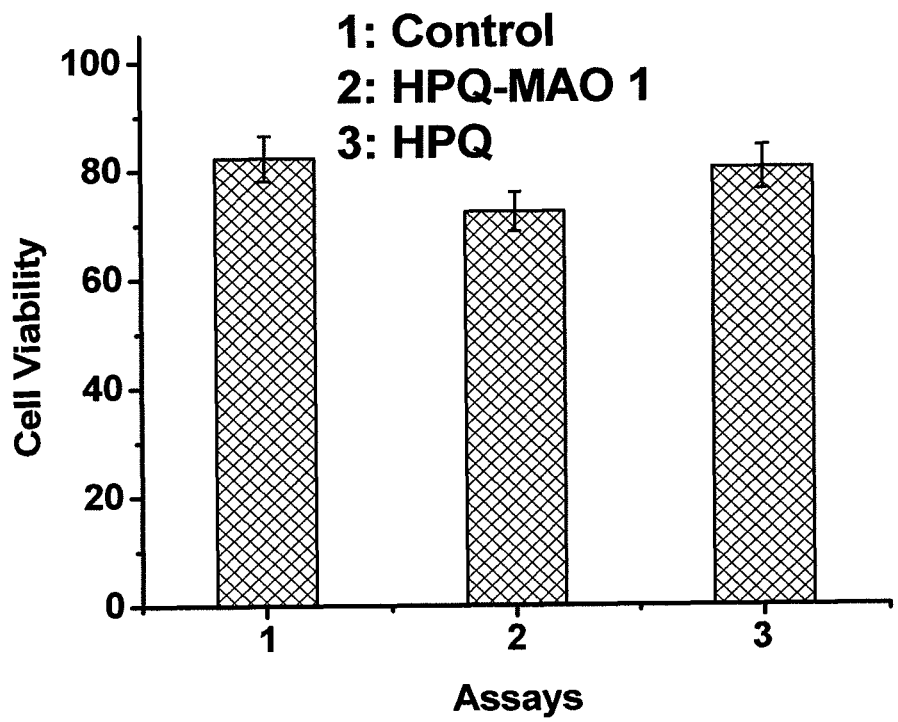
FIG. 6 illustrates the cell viability of substrate MAO-HPQ 1 (2-(5'-chloro-2'-(3-aminopropoxy)phenyl)-6-chloro-4 (3H)-quinazolinone) and 2-(2'-hydroxy-5'-chlorophenyl)-6-chloro-4(3H)-quinazolinone (indicated as HPQ") in PC12 cell line. As a Control, cells were treated with 5% of DMSO only.

Cell Viability Assays the cytotoxicity activity of MAO-HPQ 1 was evaluated by the standard MTT assay as previously described in Y. H. Choi et al, *J. Control. Rel.*, 1998, 54, 39-48. MAO-HPQ 1 indicates less toxicity and thereby can be used as a probe for real-time imaging of MAO activity in living cells (FIG. 6).

Example 7

In Vitro Enzyme Inhibition Assays

Figure 5:
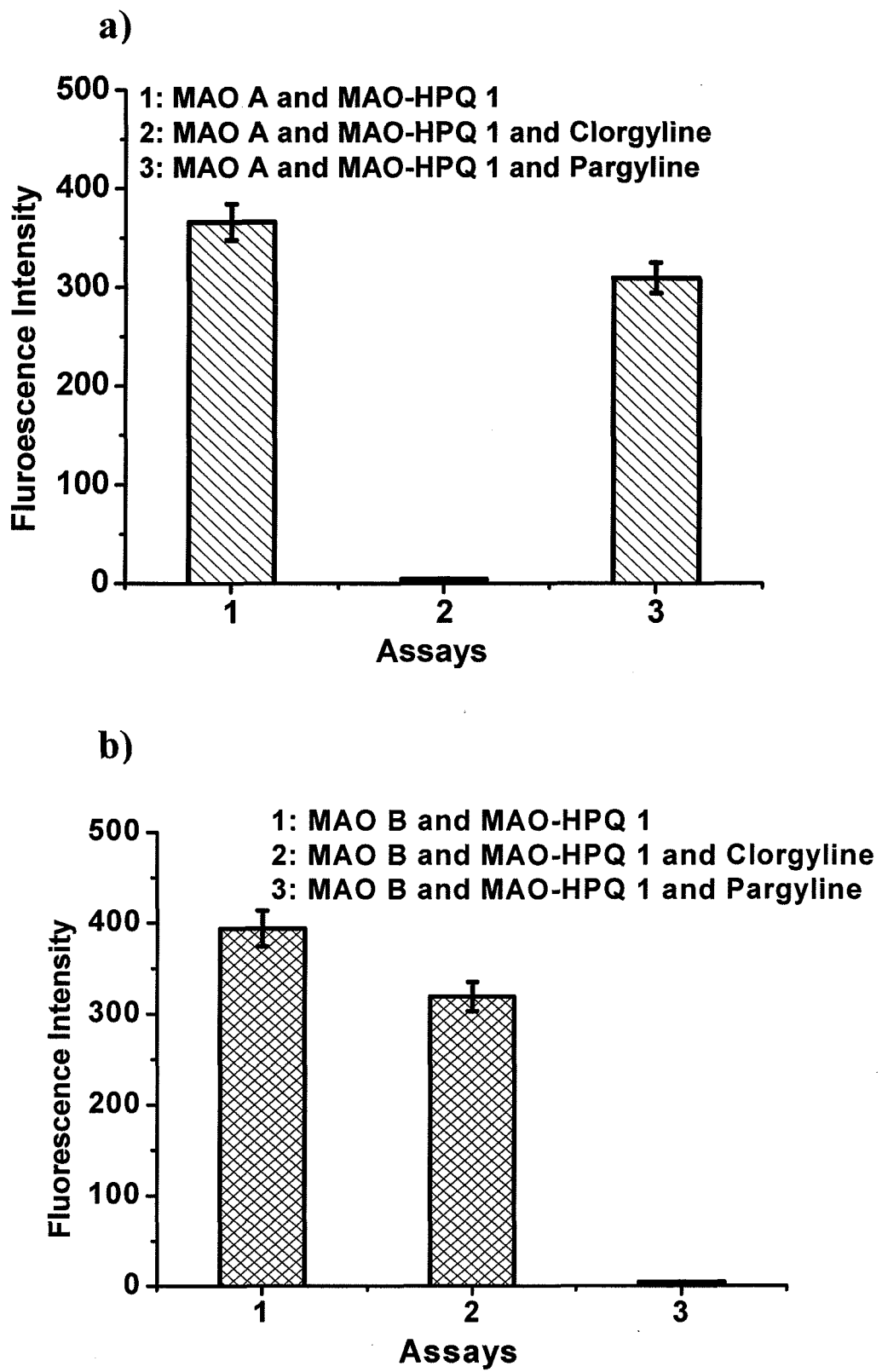
FIG. 5 illustrates enzyme inhibition measurements of MAO and HPQ-MAO 1 (2-(5'-chloro-2'-(3-aminopropoxy) phenyl)-6-chloro-4(3H)-quinazolinone) when tested with inhibitor Clorgyline or Pargyline.

MAO A and B isoforms were separately pretreated with clorgyline and pargyline (200 μM) respectively for 2 hours then incubated with MAO-HPQ 1 (200 μM) for another 2 hours for fluorescent detection (FIG. 5). In addition, the native enzyme activity in cultured cells was also detected with this probe.

Example 8

Imaging of Monoamine Oxidase Activity in Living Cells

PC12 cell (*Rattus norvegicus*, adrenal gland) was bought from American Type Culture Collection (ATCC Cat No: CR-1721) and maintained in F-12K medium (ATCC, Manassas Va.) containing 10% FBS (Invitrogen, Burlington, Canada). PC12 cell line were seeded at a density of $2\times10^5$ in a 35 mm diameter μ-dish plastic bottom (ibidi GmbH, Germany) and cultured for 2 days with Nerve Growth Factor (2.5S, 30 ng/mL, Invitrogen, Carlsbad, Calif.)[2] in Dulbecco's Modified Eagle Medium (DMEM 1×, without phenol red, Gibco/Invitrogen, Carlsbad, Calif.) containing 4.5 g/L D-glucose, 2 mM GlutaMax-1 (Invitrogen). Control C6 glioma cell line was bought from American Type Culture Collection (ATCC Cat No.: CCL-107) and cultured with the same protocol as PC12 cell lines). After 2 days of culture, the live PC12 and C6 glioma cell lines were washed twice with DMEM. The live cells were then treated separately with 100 μM of MAO-HPQ 1 in DMEM (containing 0.5% of DMSO) and incubated for 1 hour in an incubator at 37° C. The cells were washed twice with Hank's Balanced Salt solution (Sigma). The fluorescence imaging was acquired with a Confocal fluorescence microscope (Nikon, Eclipse TE2000-E) using a super high pressure mercury lamp (Nikon, TE2-PS100W) with excitation filter: 360/40 nm; emission filter: 535/40 nm.

In the inhibition investigation, the live PC12 cell lines were washed twice with DMEM and pre-treated separately with 100 μM Clorgyline and Pargyline in DMEM for 1 hour in an incubator at 37° C. MAO-HPQ 1 was then added to the μ-dish with the final concentration of 100 μM and incubated for another 1 hour at 37° C. The cells were then washed twice with Hank's Balanced Salt solution. The fluorescence imaging was acquired with the Confocal fluorescence microscope.

Figure 4:
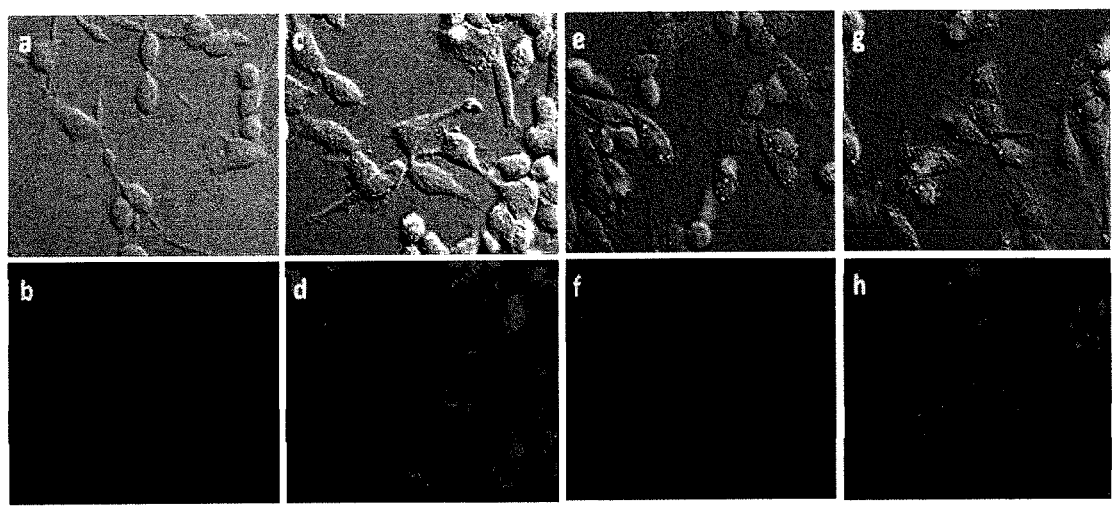
FIG. 4 represents normal light (top panel) and fluorescence contrast (bottom panel) images of C6 Glioma Cells and PC12 cells with 100 µM MAO-HPQ-1 (2-(5'-chloro-2'-(3-aminopropoxy)phenyl)-6-chloro-4(3H)-quinazolinone) incubated at 37° C. for 60 minutes. (a) Normal light C6 and MAO-HPQ-1. (b) Fluorescence images of C6 and MAO-HPQ-1. (c) Normal light PC12 and MAO-HPQ-1. (d) Fluorescence images of C6 and MAO-HPQ-1. (e) Normal light PC12, Clorgyline (MAO A-inhibitor) and MAO-HPQ-1. (f) Fluorescent Images of PC12, Clorgyline and MAO-HPQ-1. (g) Normal light PC12, Pargyline and MAO-HPQ-1 (h) Fluorescence images of Pargyline (MAO B-inhibitor) and MAO-HPQ-1. All fluorescence were corrected with back ground substraction.

The real time imaging of MAO activities in living cells was demonstrated using MAO-HPQ 1. PC12 cell line was chosen owing to its high expression of MAO. As a negative control, C6 glioma cells were used as there is no MAO expression in this cell line. Both C6 glioma cells and PC12 cells were cultured and incubated with 100 μM of MAO-HPQ 1 at 37° C. for 1 h. Live cell imaging results indicated a clear difference: the PC12 cells emitted bright fluorescence signals, whereas little 2-(2'-hydroxy-5'-chlorophenyl)-6-chloro-4(3H)-quinazolinone fluorescence was observed in C6 glioma cells, as shown in FIG. 4, demonstrating the fact that MAO-HPQ 1 was able to image the MAO activity in high MAO-expressing PC12 cells.

Further imaging investigations were conducted by utilizing two commonly used inhibitors: Clorgyline for MAO A and Pargyline for MAO B. The PC12 cells were pre-treated separately with 100 μM of MAO A inhibitor clorgyline and MAO B inhibitor pargyline, and then incubated with 100 μM of MAO-HPQ probe 1 at 37° C. for 1 h. The imaging data revealed that there was no obvious fluorescence in clorgyline pre-treated PC12 cells, indicating the significant enzyme inhibition in the living cells (FIG. 4e). However, the PC12 cells pre-treated with MAO B inhibitor, pargyline, still displayed strong fluorescence similar to the imaging result without inhibitor treatment, demonstrating that MAO activity remains in the cell. These results implied that PC12 cells mainly express MAO A enzyme and that its activity could be selectively suppressed by clorgyline rather than pargyline. This is in accordance with the in vitro enzyme inhibition tests (FIG. 5). MAO-HPQ 1 indicates less toxicity (FIG. 6) and thereby can be used as a new probe for real-time imaging of MAO activity in living cells.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

What is claimed is:

1. A compound of general formula (I)

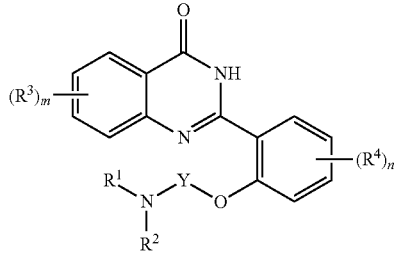

or a salt, tautomer or stereoisomer thereof,
wherein
$R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl;

each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_6$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR';

Y is an aliphatic group;
R and R' are independently selected from the group consisting of hydrogen and unsubstituted $C_1$-$C_4$ alkyl; and
m and n are integers independently selected from 1, 2, 3 and 4.

2. The compound of claim 1, wherein the aliphatic group is a straight or branched hydrocarbon chain.

3. The compound of claim 1, wherein Y is substituted or unsubstituted $C_1$-$C_{10}$ alkyl.

4. The compound of claim 3, wherein Y is substituted or unsubstituted methyl, ethyl, n-propyl, n-butyl, n-pentyl, or n-hexyl.

5. The compound of claim 4, wherein Y is unsubstituted n-propyl.

6. The compound of claim 1, wherein n, m or both are 1.

7. The compound of claim 6, wherein $R^3$ and $R^4$ or both are independently selected from the group consisting of hydrogen, halogen, unsubstituted or substituted $C_1$-$C_{10}$ alkyl and unsubstituted or substituted $C_1$-$C_{10}$ alkoxy.

8. The compound of claim 6, wherein $R^3$, $R^4$, or both are independently halogen.

9. The compound of claim 6, wherein $R^3$ is in the 6-position of the quinazolinone ring.

10. The compound of claim 6, wherein $R^4$ is in the 5-position of the phenyl ring.

11. The compound of claim 1, wherein $R^1$ and $R^2$ are independently selected from the group consisting of hydrogen and unsubstituted or substituted $C_1$-$C_4$ alkyl.

12. The compound of claim 1, wherein the compound is selected from the group consisting of:

2-(5'-chloro-2'-(3-aminopropoxy)phenyl)-6-chloro-4 (3H)-quinazolinone;

2-(5'-chloro-2'-(3-(N-methylamino)propoxy)phenyl)-6-chloro-4(3H)-quinazolinone; and 2-(5'-chloro-2'-(3-(N,N'-dimethylamino)propoxy)phenyl)-6-chloro-4(3H)-quinazolinone.

13. A method for determining the presence, amount or activity of a monoamine oxidase comprising:
i) contacting at least one compound according to claim 1 with the monoamine oxidase under conditions that allow the oxidative deamination of the compound by the monoamine oxidase; and
ii) determining the fluorescence of the compound.

14. The method of claim 13, wherein the presence, amount or activity of a monoamine oxidase is determined in a biological sample.

15. The method of claim 14, wherein the biological sample is derived from a mammal.

16. The method of claim 13, wherein the presence, amount or activity of a monoamine oxidase is determined in a cell.

17. The method of claim 13, wherein the monoamine oxidase is selected from the group consisting of monoamine oxidase A (MAO A) and monoamine oxidase B (MAO B).

18. A method of preparing the compound of general formula (I) according to claim 1 comprising: reacting a compound of general formula (II)

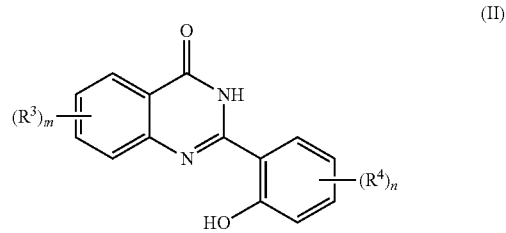

or a salt, tautomer or stereoisomer thereof,
wherein each $R^3$ and $R^4$ is independently selected from the group consisting of hydrogen, halogen, cyano, nitro, sulfonyl, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted $C_1$-$C_{10}$ alkoxy, unsubstituted or substituted $C_3$-$C_8$ cycloalkyl, unsubstituted or substituted $C_3$-$C_8$ cycloalkoxy, unsubstituted or substituted $C_6$-$C_{14}$ aryl, unsubstituted or substituted 5- to 10-membered heteroaryl wherein 1 to 4 ring atoms are independently selected from nitrogen, oxygen or sulphur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR';

R and R' are independently selected from the group consisting of hydrogen and unsubstituted $C_1$-$C_4$ alkyl; and m and n are integers independently selected from 1, 2, 3 and 4;

with a compound of general formula (III)

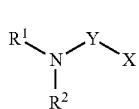 (III)

wherein $R^1$ and $R^2$ are independently selected from the group consisting of hydrogen, unsubstituted or substituted $C_1$-$C_{10}$ alkyl, unsubstituted or substituted $C_2$-$C_{10}$ alkenyl, and unsubstituted or substituted $C_2$-$C_{10}$ alkynyl;

Y is an aliphatic group; and

X is halogen;

in the presence of a base to form an intermediate; and reacting the intermediate with trifluoracetic acid and tri-isopropylsilane.

\* \* \* \* \*